United States Patent [19]
Davis et al.

[11] Patent Number: 5,721,245
[45] Date of Patent: Feb. 24, 1998

[54] 4-[3-INDOLYL]-1H-PYRROLONE

[75] Inventors: Peter David Davis, Letchworth; Christopher Huw Hill, Knebworth; Geoffrey Lawton, Hitchin, all of England

[73] Assignee: Hoffmann-La Roche Inc., Nutley, N.J.

[21] Appl. No.: 373,681

[22] Filed: Jan. 17, 1995

Related U.S. Application Data

[63] Continuation of Ser. No. 823,215, Jan. 21, 1992, abandoned, which is a continuation of Ser. No. 479,823, Feb. 14, 1990, abandoned.

[30] Foreign Application Priority Data

Feb. 23, 1989 [GB] United Kingdom ............... 8904161
Dec. 13, 1989 [GB] United Kingdom ............... 8928210

[51] Int. Cl.$^6$ ............. A61K 31/44; C07D 471/04; C07D 405/00; C07D 487/00
[52] U.S. Cl. ............. 514/294; 514/411; 514/414; 514/418; 546/94; 548/428; 548/455; 548/456
[58] Field of Search ............. 546/94; 514/294, 514/411, 414, 418; 548/428, 455, 456

[56] References Cited

U.S. PATENT DOCUMENTS

| | | | |
|---|---|---|---|
| 3,317,524 | 5/1967 | Freed et al. | 544/80 |
| 4,107,297 | 8/1978 | Omura et al. | 424/122 |
| 5,057,614 | 10/1991 | Davis et al. | 548/466 |

OTHER PUBLICATIONS

Chem.Abstr. 109-73718u (Tetrahedron Lett. 1987, 28/38) pp.4441-4444.
Chem.Abstr. 109, 128754k (J.Prokt.Chem. 1987) 329(4), 599-606.
Chem.Abstr. 104-207579g (Tetrahedron Lett. 1985) 26(34), 4015-18.
Chem.Abstr. 101-55460j (Heterocycles 1984) 21(1), 309-24.
Chem. Abstr. 102-6236c (J.Prokt.Chem. 1984) 326(4) 594-8.
Chem. Abstr. 98-215863t (Heterocycles 1983) 20(3) 469-76.
Chem. Abstr. 93-66027r (Angeu. Chem.) 42(6) 463-4 (1979).
Chem. Abstrs. Eleventh Collective Index vols. 96-105, p. 59203cs (1982-1986).
Int. J. Cancer 43:841 (1989) T. Meyer et al.
J. Heterocyclic Chem. 21 (1984) pp. 623-624, Crenshaw et al.
J. Med. Chem. 8(1965) p. 700, Remers et al.
J. Amer. Che. Soc. 60, (1938) p. 2414, Bayer et al.
J. Amer. Chem. Soc. 96, (1974) p. 3966, Coffen et al.
J. Amer. Chem. Soc. (1964) Hallas et al.
J. of Pharmacology and Experimental Therapeutics, 268:922-929 (1994) A. Birchall, et al.
Drugs of the Future 18(8) 727-735 (1993) W. Harris, et al.
Agents Action 38:135-147 (1993) D. Bradshaw et al.
Clin. Exp. Immunol. 46:185-195 (1981) P. Fitzharris et al.
Scand. J. Immunol. 31, 208(1990) J. Woo et al.
J. Nat. Cancer Instit. 51:1409 (1973) H.D. Soule et al.
Nature, 270:347-349 (1977) S.J. Collins et al.
Int.J.Cancer 17: 565 (1975) C. Sundstrom et al.
AIDS 3:101 (1989) D. Kinchington et al.
J. Med. Chem. 33:2137 (1990) J.A. Martin et al.
Biochem. Biophys. Res. Commun. 171:1087 (1990) B. Twomey et al.
Inflammation 8:209(1984) J.C. Gay et al.
Antiviral Research 13:273 (1990) E. Matthes et al.
Int. J. Cancer 43:851 (1989) T. Meyer et al.
Biochem. Biophys Res. Commun. vol. 91 No. 4 pp. 1218-1224 (1979).
EMBO Journal vol. 9 No. 4 pp. 1165-1170 (1990) Jakobovits, et al.

Primary Examiner—Alan L. Rotman
Attorney, Agent, or Firm—George W. Johnston; Patricia S. Rocha-Tramaloni; Robert A. Silverman

[57] ABSTRACT

A compound of the formula

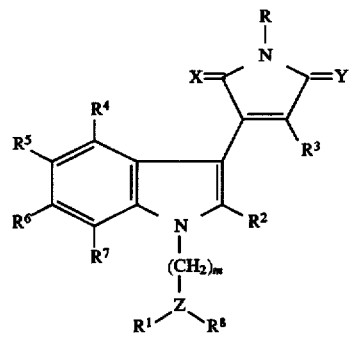

wherein R is hydrogen or hydroxy, $R^1$ and $R^2$ taken together are a group of the formula —$(CH_2)_m$— and $R^7$ is hydrogen or $R^1$ and $R^7$ taken together are a group of the formula —$(CH_2)_n$— and $R^2$ is hydrogen; $R^3$ is an aryl or aromatic heterocyclic group; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, a 5- or 6-membered saturated nitrogen-containing heterocycle; X and Y are oxygen; Z is CH; m, p and q are, independently, an integer from 0 to 5, and n an integer from 1 to 5, as well as pharmaceutically acceptable salts thereof which are useful in the control of inflammatory, immunological, oncological, bronchopulmonary or cardiovascular disorders.

18 Claims, No Drawings

4-[3-INDOLYL]-1H-PYRROLONE

This is a continuation, of application Ser. No. 07/823,215, filed Jan. 21, 1992, which is a Rule 60 Continuation of Ser. No. 07/479,823, filed Feb. 14, 1990, both now abandoned.

BRIEF SUMMARY OF THE INVENTION

The invention relates to substituted pyrroles. More particularly, the invention relates compounds of the formula

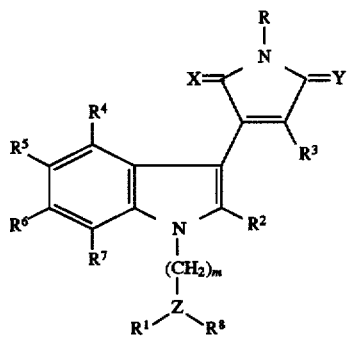

wherein R is hydrogen or hydroxy, $R^1$ and $R^2$ taken together are a group of the formula —$(CH_2)_n$— and $R^7$ is hydrogen or $R^1$ and $R^7$ taken together are a group of the formula —$(CH_2)_n$— and $R^2$ is hydrogen; $R^3$ is an aryl or aromatic heterocyclic group; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkyl amino, dialkylamino, trialkylamino, azido, acylamino, alkylsulfonylamino, arylsulfonylamino, alkylthio, alkoxycarbonylamino, aminoacylamino, aminocarbonylamino, isothiocyanato, alkylcarbonyloxy, alkylsulfonyloxy or arylsulfonyloxy, a 5- or 6-membered saturated nitrogen-containing heterocycle attached via the nitrogen atom or a group of the formula —U—C(V)—W; U is S or NH; V is NH, $NNO_2$, NCN, $CHNO_2$; W is amino, monoalkylamino or dialkylamino; one of X and Y is O and the other is O or (H,H); Z is CH or N; m, p and q are, independently, an integer from 0 to 5, and n is an integer from 1 to 5, with the proviso that q and m are, independently, 2 to 5 when Z is N;

as well as pharmaceutically acceptable salts of acidic compounds of formula I with bases and of basic compounds of formula I with acids.

The compounds of formula I are useful in the control or prevention of illnesses, especially in the control or prevention of inflammatory, immunological, oncological, bronchopulmonary and cardiovascular disorders or in the treatment of asthma or AIDS.

In another aspect, the invention relates to processes for the preparation of the compounds of formula I, pharmaceutical compositions containing compounds of formula I, uses thereof and intermediates.

DETAILED DESCRIPTION OF THE INVENTION

The invention relates to substituted pyrroles. More particularly, the invention relates compounds of the formula

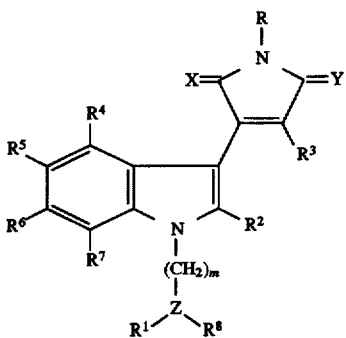

wherein R is hydrogen or hydroxy, $R^1$ and $R^2$ taken together are a group of the formula —$(CH_2)_n$— and $R^7$ is hydrogen or $R^1$ and $R^7$ taken together are a group of the formula —$(CH_2)_n$— and $R^2$ is hydrogen; $R^3$ is an aryl or aromatic heterocyclic group; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, alkoxycarbonylamino, aminoacylamino, aminocarbonylamino, isothiocyanato, alkylcarbonyloxy, alkylsulfonyloxy or arylsulfonyloxy, a 5- or 6-membered saturated nitrogen-containing heterocycle attached via the nitrogen atom or a group of the formula —U—C(V)—W; U is S or NH; V is NH, $NNO_2$, NCN, $CHNO_2$; W is amino, monoalkylamino or dialkylamino; one of X and Y is O and the other is O or (H,H); Z is CH or N; m, p and q are, independently, an integer from 0 to 5, and n is an integer from 1 to 5, with the proviso that q and m are, independently, 2 to 5 when Z is N;

as well as pharmaceutically acceptable salts of acidic compounds of formula I with bases and of basic compounds of formula I with acids.

Objects of the invention are the compounds of formula I and their aforementioned salts and as therapeutically active substances; a process for the preparation of said compounds and salts and intermediates useful in said process; medicaments containing said compounds and salts and the preparation of these medicaments; and the use of said compounds and salts in the control or prevention of illnesses, especially in the control or prevention of inflammatory, immunological, oncological, bronchopulmonary and cardiovascular disorders or in the treatment of asthma or AIDS, or for the preparation of a medicament against inflammatory, immunological, oncological, branchopulmonary and cardiovascular disorders or against asthma or AIDS.

As used herein, the term "alkyl", alone or in combination, denotes a straight-chain or branched-chain alkyl group containing 1 to 7, preferably a 1 to 4, carbon atoms, such as methyl, ethyl, propyl, isopropyl, butyl, sec.butyl, tert.butyl, pentyl and the like. The term "alkoxy", alone or in combinations, denotes an alkyl group as defined earlier which is attached via an oxygen atom, examples of alkoxy groups are methoxy, ethoxy, propoxy, isopropoxy, butoxy, tert.butoxy and the like. A haloalkyl group can carry one or more halogen atoms, examples of such groups are chloromethyl, trifluoromethyl and the like. The term "acyl" denotes an acyl group derived from an alkanoic acid containing 1 to 7, preferably 1 to 4, carbon atoms, for example, formyl acetyl, propionyl, butyryl and the like), or from an aromatic carboxylic acid, for example, benzoyl and the like. The term "aryl", alone or in combination, denotes a monocyclic or polycyclic group, preferably a monocyclic or bicyclic group, for example, phenyl or naphthyl, which can be substituted or unsubstituted, for example, with one or more, preferably with one to three, substituents, selected from halogen, alkyl, hydroxy, alkoxy, haloalkyl, nitro, amino, acylamino, alkylthio, alkylsulfinyl and alkylsulfonyl. Examples of such aryl groups are phenyl, 2-chlorophenyl, 3-chlorophenyl, 4-chlorophenyl, 3-bromophenyl, 2-methylphenyl, 3-methylphenyl, 2,5-dimethylphenyl, 4-methoxyphenyl, 2-trifluoromethylphenyl, 3-trifluoromethylphenyl, 2-nitrophenyl, 3-nitrophenyl, 4-nitrophenyl, 3-aminophenyl, 4-aminophenyl, 4-methylthiophenyl, 4-methylsulfinylphenyl, 4-methylsulfonylphenyl, 1-naphthyl, 2-naphthyl and the like. The term "aromatic heterocyclic" means a 5-membered or 6-membered heterocyclic aromatic group which can optionally carry a fused benzene ring and which can be substituted or unsubstituted, for example with one or more, preferably one to three, substituents selected from halogen, alkyl, hydroxy, alkoxy, haloalkyl, nitro, amino, acylamino, alkylthio, alkylsulfinyl and alkylsulfonyl. Examples of such heterocyclic groups are 2-thienyl, 3-thienyl, 3-benzothienyl, 3-benzofuranyl, 2-pyrrolyl, 3-indolyl and the like which can be unsubstituted or substituted in the manner indicated. The 5- or 6-membered saturated nitrogen-containing heterocycle attached via the nitrogen atom can contain an additional nitrogen or oxygen or a sulfur atom, examples of such heterocycles are pyrrolidino, piperidino, piperazino, morpholino and thiamorpholino. The term "halogen" denotes fluorine, chlorine, bromine or iodine.

The compounds of formula I in which Z is CH and $R^8$ is a group of the formula —$(CH_2)_p$—$R^9$ in which p is an integer from 1 to 5 or —$(CH_2)_q$—$R^{10}$ contain an asymmetric carbon atom and can therefore exist in the racemic or optically active form. The invention includes within its scope not only the racemic compounds, but also the optically active isomers, that is, the enantiomers.

In preferred classes of compounds of formula I, $R^1$ and $R^2$ taken together are —$CH_2$— and $R^7$ is hydrogen, m stands for 1 or 2 and Z is CH; or $R^1$ and $R^2$ taken together are —$(CH_2)_2$— and $R^7$ is hydrogen, m stands for 1 and Z is CH; or $R^1$ and $R^2$ taken together are —$CH_2$— and $R^7$ is hydrogen, m stands for 2 and Z is N; or $R^1$ and $R^7$ taken together are —$CH_2$— and $R^2$ is hydrogen, m stands for 1 and Z is CH; or $R^1$ and $R^7$ taken together are —$(CH_2)_2$— and $R^2$ is hydrogen, m stands for 0 and Z is CH. Preferably, $R^3$ is phenyl, naphthyl, 3-benzothienyl, 3-benzofuranyl or 3-indolyl which is optionally substituted as defined earlier, especially 1-methyl-3-indolyl. Preferably, $R^4$, $R^5$ and $R^6$ are hydrogen. Preferably, $R^8$ is a group of the formula —$(CH_2)_q$—$R^{10}$. Preferably, q stands for 1 or 2. Preferably, $R^{10}$ is hydroxy, amino, monoalkylamino, dialkylamino, trialkylamino, azido, acylamino, alkylcarbonyloxy or alkylsulfonyloxy or a group of the formula —U—C(V)—W. Preferably, U is S, V is NH and W is amino.

Especially preferred compounds provided by the invention are:

3-[8-(Aminomethyl)-6,7,8,9-tetrahydropyrido[1,2-a]indol-10-yl]-4-(1-methyl-3-indolyl)-1H-pyrrole-2,5-dione;

3-[7-(amidinothiomethyl)-6,7,8,9-tetrahydropyrido[1,2-a]indol-10-yl]-4-(1-methyl-3-indolyl)-1H-pyrrole-2,5-dione; and 3-[6,7,8,9-tetrahydro-8-[(dimethylamino)methyl]pyrido[1,2-a]indol-10-yl]-4-(1-methyl-3-indolyl)-1H-pyrrole-2,5-dione, and their pharmaceutically acceptable acid addition salts.

According to the process provided by the invention, the compounds of formula I as well as pharmaceutically acceptable salts of acidic compounds of formula I with bases and of basic compounds of formula I with acids are prepared as follows:

(a) for the preparation of a compound of formula I in which X and Y both are O, by reacting a compound of the formula

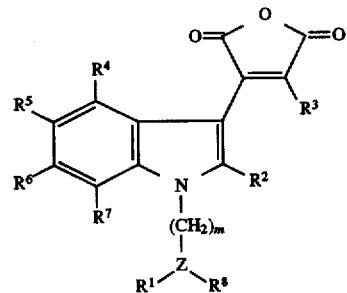

wherein
$R^1$, $R^2$, $R^3$, $R^4$, $R^5$, $R^6$, $R^7$, $R^8$, Z and m have the significance given earlier, with ammonia under pressure or with hexamethyldisilazane and methanol to give a compound of formula I in which R is hydrogen or with hydroxylamine to give a compound of formula I in which R is hydroxy, or (b) for the preparation of a compound of formula I in which one of X and Y is O and the other is (H,H), by reducing a compound of formula I in which X and Y both are O with lithium aluminum hydride, or (c) if desired, functionally modifying a reactive center present in a compound of formula I obtained, and (d) also if desired, converting an acidic compound of formula I into a pharmaceutically acceptable salt with a base or converting a basic compound of formula I into a pharmaceutically acceptable salt with an acid.

The reaction of a compound of formula II with ammonia under pressure, in accordance with embodiment (a) of the process, is conveniently carried out using aqueous ammonia (preferably 33% aqueous ammonia), in the presence of a water-miscible inert organic solvent such as dimethylformamide or the like. The reaction is preferably carried out at an elevated temperature, for example, a temperature in the range of about 100° C. to about 150° C.

The reaction of a compound of formula II with hexamethyldisilazane and methanol, also in accordance with embodiment (a) of the process, is conveniently carried out in an inert organic solvent such as a halogenated hydrocarbon, for example, chloroform, carbon tetrachloride or chlorobenzene, or an aromatic hydrocarbon, for example, benzene, toluene or a xylene, at an elevated temperature, for example, a temperature between about 40° C. and 110° C.

The reaction of a compound of formula II with hydroxylamine, also in accordance with embodiment (a) of the process, is conveniently carried out in an inert organic solvent such as dimethylformamide or the like, at room temperature or an elevated temperature, preferably at an elevated temperature, for example, about 100° C. Expediently, the hydroxylamine is used in the form of a salt such as the hydrochloride and the reaction is carried out in the presence of a base such as an alkali metal carbonate, for example, sodium or potassium carbonate.

The reduction of a compound of formula I in which X and Y both are O with lithium aluminum hydride in accordance with embodiment (b) of the process is expediently carried out in an inert organic solvent such as an aliphatic or cyclic ether, for example, diethyl ether, tetrahydrofuran and the like, at a temperature between about 0° C. and the reflux temperature of the reaction mixture.

A reactive center which is present in a compound of formula I can be modified, if desired, in accordance with embodiment (c) of the process. All of these modifications can be carried out according to known methods. For example, when $R^8$ is a group of the formula —$(CH_2)_p$—$R^9$ in which $R^9$ is alkoxycarbonyl and p stands for O, this group can be converted into a corresponding group in which $R^9$ is hydrogen by treatment with an acid. Again, for example, a group of the formula —$(CH_2)_q$—$R^{10}$ in which $R^{10}$ is alkylcarbonyloxy can be converted into a corresponding group in which $R^{10}$ is hydroxy by appropriate base treatment. A group of the formula —$(CH_2)_q$—$R^{10}$ in which $R^{10}$ is hydroxy can be converted into a corresponding group in which $R^{10}$ is amino, monoalkylamino, dialkylamino, trialkylamino or a 5- or 6-membered saturated nitrogen-containing heterocycle attached via the nitrogen atom by treatment firstly with trifluoromethanesulfonic anhydride and subsequently with ammonia, a monoalkylamine, a dialkylamine, a trialkylamine or an appropriate heterocycle, respectively.

A group of the formula —$(CH_2)_q$—$R^{10}$ in which $R^{10}$ is hydroxy can be reacted with an alkanesulfonic anhydride to give a corresponding group in which $R^{10}$ is alkylsulfonyloxy. A group of the formula —$(CH_2)_q R^{10}$ in which $R^{10}$ is alkylsulfonyloxy can be converted into a corresponding group in which $R^{10}$ is formamido by reaction with ammonia in dimethylformamide or in which $R^{10}$ is azido by reaction with an alkali metal azide or in which $R^{10}$ is a group of the formula —U—C(V)—W in which U is S, V is NH and W is amino by reaction with thiourea. Further, a group of the formula —$(CH_2)_q$—$R^{10}$ in which $R^{10}$ is azido can be converted by catalytic hydrogenation into a corresponding group in which $R^{10}$ is amino. A group of the formula —$(CH_2)_q$—$R^{10}$ in which $R^{10}$ is alkoxycarbonylamino can be converted into a corresponding group in which $R^{10}$ is amino by treatment with an acid.

A group of the formula —$(CH_2)_q$—$R^{10}$ in which $R^{10}$ is amino can be acylated to give a corresponding group in which $R^{10}$ is acylamino or can be reacted with 3,5-dimethyl-$N^2$-nitro-1-pyrazole-1-carboxamide to give a corresponding group in which $R^{10}$ is a group of the formula —U—C(V)—W wherein U is NH, V is NH and W is $NNO_2$. Further, a group of the formula —$(CH_2)_q$—$R^{10}$ in which $R^{10}$ is amino can be converted into a corresponding group in which $R^{10}$ is isothiocyanato by reaction with 1,1-thiocarbonyldiimidazole. A group of the formula —$(CH_2)_p$—$R^9$ in which $R^9$ is cyano can be treated with hydrogen chloride and subsequently with ammonia to give a corresponding group in which $R^9$ is amidino. Again, for example, a compound of formula I in which Z is N and $R^8$ is a group of the formula —$(CH_2)_p$—$R^9$ wherein p stands for O and $R^9$ is hydrogen can be converted into a corresponding compound in which $R^9$ is alkylcarbonyl, alkoxycarbonyl or aralkoxycarbonyl by appropriate acylation, into a corresponding compound in which $R^9$ is alkylsulfonyl by reaction with an alkanesulfonyl chloride, into a corresponding compound in which $R^9$ is aminoalkylcarbonyl by treatment with a trifluoroacetamidoalkanoyl chloride and subsequent reaction with ammonia, into a corresponding compound in which $R^9$ is aminocarbonyl by treatment with 1,1-carbonyldiimidazole and subsequent reaction with ammonia or into a corresponding compound in which $R^9$ is aminothiocarbonyl by treatment with 1,1-thiocarbonyldiimidazole and subsequent reaction with ammonia. It will be appreciated that the foregoing modifications are given by way of example only and that other modifications within the purview of a person skilled in the art are also possible.

The conversion of an acidic compound of formula I into a pharmaceutically acceptable salt in accordance with embodiment (d) of the process can be carried out by treatment with a suitable base in a known manner. Suitable salts are those derived not only from inorganic bases, for example, sodium hydroxide, potassium hydroxide, calcium hydroxide and the like, but also from organic bases such as ethylenediamine, monoethanolamine, diethanolamine and the like. The conversion of a basic compound of formula I into a pharmaceutically acceptable salt, also in accordance with embodiment (d) of the process, can be carried out by treatment with a suitable acid in a known manner. Suitable salts are those derived not only from inorganic acids, for example, hydrochloric acid, hydrobromic acid, phosphoric acid, sulfuric acid and the like, but also from acetic acid, citric acid, fumaric acid, tartaric acid, maleic acid, methanesulfonic acid, p-toluenesulfonic acid and the like.

The compounds of formula II which are used as starting materials in embodiment (a) of the process form part of the invention. They can be prepared by reacting a compound of the formula

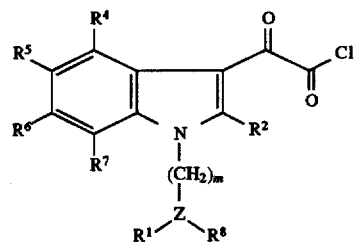

wherein R, R, $R^4$, $R^5$, $R^6$, $R^7$, $R^8$, Z and m have the significance given earlier, with a compound of the formula

HOOC—$CH_2$—$R^3$      IV wherein $R^3$ has the significance given earlier, and, where required, functionally modifying a reactive center present in a compound of formula II obtained.

The reaction of a compound of formula III with a compound of formula IV is preferably carried out in the presence of an acid-binding agent, expediently a tertiary amine such as a trialkylamine, for example, triethylamine, diisopropylethylamine and the like, and in an inert organic solvent such as a halogenated aliphatic hydrocarbon, for example, dichloromethane and the like, at about room temperature.

The optional functional modification of a reactive substituent present in a compound of formula II can be carried out in the same manner as described earlier in connection with the functional modification of a reactive center present in a compound of formula I.

The compounds of formula III can be prepared, in turn, by reacting a compound of the formula

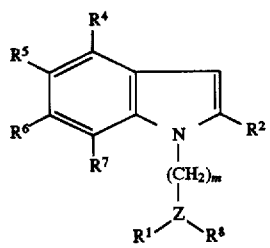

wherein $R^1$, $R^2$, $R^4$, $R^5$, $R^6$, $R^7$, $R^8$, Z and m have the significance given earlier, with oxalyl chloride, conveniently in an inert organic solvent such as a halogenated aliphatic hydrocarbon, for example, dichloromethane and the like, at a temperature from about 0° C. to the reflux temperature of the solvent. The resulting compound of formula III can be reacted in situ with the compound of formula IV or can be isolated and purified, for example, by concentration followed by crystallization, prior to the reaction with the compound of formula IV.

The compounds of formula V hereinbefore are known compounds or analogues of known compounds which can be prepared in a similar manner to the known compounds. Further, certain of the Examples hereinafter contain detailed information containing the preparation of the respective starting materials.

The compounds of formula I and their pharmaceutically acceptable salts are protein kinase inhibitors; they inhibit cellular processes, for example cell proliferation, and can be used in the control or prevention of illnesses, for example in the control or prevention of inflammatory disorders such as arthritis, immune diseases, in conjunction with organ transplants and also in oncology. They inhibit infection of cells with human immunodeficiency virus and are thus useful in the treatment of AIDS. The compounds and salts of the invention also inhibit smooth muscle contraction and can therefore be used against cardiovascular and bronchopulmonary disorders. Further, they are also useful in asthma therapy.

The activity of the compounds in inhibiting protein kinase C can be demonstrated by means of the in vitro assay system described, for example, in Biochemical and Biophysical Research Communications 19 (1979) 1218.

The $IC_{50}$ FIGURES in the following Table are that concentration of test compound which reduces by 50% the protein kinase-induced incorporation of $^{32}P$ from $[\gamma\text{-}^{32}P]$ ATP into histone.

TABLE

| Compound | $IC_{50}$ |
|---|---|
| 3-[8-(Aminomethyl)-6,7,8,9-tetrahydro-pyrido[1,2-a]indol-10-yl]-4-(1-Methyl-3--indolyl)-1H-pyrrole-2,5-dione hydrochloride | 8 nM |
| -3-[7-Aminomethyl)-6,7,8,9-tetrahydro-pyrido[1,2-a]indol-10-yl]-4-(1-methyl-3-indolyl)-1H-pyrrole-2,5-dione | 15 nM |
| 3-[2-(Aminoacetyl)-1,2,3,4-tetrahydro-pyrazino[1,2-a]indol-10-yl]-4-(1-methyl--3-indolyl)-1H-pyrrole-2,5-dione hydrochloride | 50 nM |
| 3-[7-(2-Aminoethyl)-6,7,8,9-tetrahydro-pyrido[1,2-a]-indol-10-yl]-4-(1-methyl--3-indolyl)-1H-pyrrole-2,5-dione hydrochloride | 20 nM |
| 3-[6,7,8,9-Tetrahydro-8-[(1-piperidino)- | 30 nM |

TABLE-continued

| Compound | $IC_{50}$ |
|---|---|
| methyl]pyrido[1,2-a]indol-10-yl]-4-(1--methyl-3-indolyl)-1H-pyrrole-2,5-dione | |
| 3-[2,3-Dihydro-2-(dimethylaminomethyl)--1H-pyrrolo[1,2-a]indol-9-yl]-4-(1-methyl--3-indolyl)-1H-pyrrole-2,5-dione trifluoro-methanesulfonate | 20 nM |
| 3-[8-Amidino-6,7,8,9-tetrahydropyrido-[1,2-a]indol-10-yl]-4-(1-methyl-3--indolyl)-1H-pyrrole-2,5-dione hydrochloride | 60 nM |
| 3-[7-(Amidinothiomethyl)-6,7,8,9-tetra-hydropyrido[1,2-a]indol-10-yl]-4--(1-methyl-3-indolyl)-1H-pyrrole-2,5-dione methanesulfonate | 10 nM |

The compounds of formula I and their aforementioned salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. However, they can also be administered rectally, for example, in the form of suppositories, or parenterally, for example, in the form of injection solutions.

For the preparation of pharmaceutical preparations, the compounds of formula I and their aforementioned salts can be formulated with therapeutically inert, inorganic or organic carriers. Lactose, maize starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are, however, generally required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerin, vegetable oils and the like. Suitable carriers for suppositories are, for example, natural or hardened oils, waxes, fats, semi-liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Medicaments containing a compound of formula I or a salt thereof as defined above and a therapeutically inert carrier as well as a process for the preparation of such medicaments are also objects of the invention. This process comprises bringing a compound of formula I or a salt thereof as defined above into a galenical administration form together with a therapeutically inert carrier material and, if desired, one or more other therapeutically active substances.

As mentioned above, the compounds of formula I and their aforementioned salts can be used in the control or prevention of illnesses, especially in the control or prevention of inflammatory, immnunological, broncho-pulmonary and cardiovascular disorders or for the treatment of asthma or of AIDS. The dosage at which a compound of formula I can be administered can vary within wide limits and will, of course, be adjusted to the individual requirements in each case. In general, in the case of oral administration to adults, a daily dosage of about 5 mg to about 500 mg should be appropriate, although the upper limit may be exceeded when this is found to be expedient. The daily dosage can be administered as a single dose or in divided doses.

The following Examples further illustrate the invention.

EXAMPLE 1

A solution of 2.90 g of 3-[8-(acetoxymethyl)-6,7,8,9-tetrahydropyrido[1,2-a]indol-10-yl]-4-(1-methyl-3-indolyl)furan-2,5-dione in 30 ml of dimethylformamide and 23 ml of 33% aqueous ammonia was heated to 140° C. for 7 hours. The mixture was extracted with ethyl acetate and the combined organic extracts were washed with water, dried over anhydrous sodium sulfate and evaporated to dryness. Crystallization of the residue from ethyl acetate gave 1.87 g of 3-[6,7,8,9-tetrahydro-8-(hydroxymethyl)pyrido-[1,2-a]indol-10-yl]-4-(1-methyl-3-indolyl)-1H-pyrrole-2,5-dione in the form of a red solid of melting point 262°–263° C.

The furandione starting material was prepared as follows:

a) A solution of 25 g of ethyl indole-2-carboxylate in 400 ml of dimethylformamide was added to a stirred solution of 5.5 g of a 60% dispersion of sodium hydride in mineral oil in 40 ml of dimethylformamide under a nitrogen atmosphere. Then, 30.9 g of ethyl bromobutyrate were added dropwise to the mixture at 0° C. and the resulting mixture was stirred at room temperature for 18 hours. The reaction was quenched with 100 ml of water and 30 ml of 2M hydrochloric acid and the mixture was extracted with dichloromethane. The combined organic extracts were washed with water, dried over anhydrous sodium sulfate and evaporated to give 49 g of an oil. This oil was dissolved in ethyl acetate and the solution was washed with water, dried over anhydrous sodium sulfate and evaporated to give 39 g of an oil. This oil was added dropwise to a stirred suspension of 20.5 g of potassium t-butoxide in 750 ml of tetrahydrofuran under a nitrogen atmosphere. After 1 hour, 200 ml of water and then 92 ml of 2M hydrochloric acid were added. The mixture was concentrated and the resulting precipitate was filtered off and dried to give 25.3 g of ethyl 6,7-dihydro-9-hydroxypyrido[1,2-a]indole-8-carboxylate. A sample was crystallized from methanol and gave crystals of melting point 101°–103° C.

b) A suspension of 19.4 g of the carboxylate of a) and 16 spoon spatula measures of Raney nickel in 480 ml of ethanol and 240 ml of water was heated to reflux for 3.5 hours. An additional 4 spoon spatula measures of Raney nickel were then added and the mixture was heated to reflux for an additional 1.5 hours. The supernatant was decanted and the catalyst was washed with ethyl acetate. The combined organic phases were concentrated and the precipitate was filtered off and dried to give 16.3 g of ethyl 6,7,8,9-tetrahydropyrido[1,2-a]indole-8-carboxylate. A sample was crystallized from methanol to give a solid of melting point 70°–72° C.

c) 16.2 g of the carboxylate of b) in 200 ml of tetrahydrofuran were added to a suspension of 2.00 g of lithium aluminum hydride in 600 ml of tetrahydrofuran at 0° C. under a nitrogen atmosphere. After 0.5 hour, the reaction was quenched by the successive additions of ethyl acetate, water and 2M hydrochloric acid and the mixture was extracted with diethyl ether. The combined organic extracts were dried and evaporated. Crystallization of the residue from diethyl ether/n-hexane gave 11.5 g of 6,7,8,9-tetrahydro-8-(hydroxymethyl)pyrido[1,2-a]indole of melting point 110°–111° C.

d) 11.4 g of acetic anhydride were added to a solution of 11.0 g of the pyridoindole from c) in 100 ml of pyridine and the resulting solution was stirred under a nitrogen atmosphere for 18 hours. The majority of the pyridine was removed by evaporation and the residue was acidified with 2M hydrochloric acid. The mixture was extracted with diethyl ether and the combined extracts were washed with sodium bicarbonate solution and with water. The extracts were dried and evaporated to dryness to give 11.25 g of 8-(acetoxymethyl)-6,7,8,9-tetrahydropyrido[1,2-a]indole of melting point 63°–64° C.

e) 4.13 g of oxalyl chloride were added dropwise to a solution of 8.2 g of the tetrahydropyridoindole of d) in 160 ml of diethyl ether under a nitrogen atmosphere. After 10 minutes, the solvent was removed under reduced pressure and the residue was dissolved in 330 ml of dichloromethane. Then, 6.34 g of 1-methyl-3-indolylacetic acid and 9.20 ml of triethylamine were added to this solution and the mixture was stirred overnight. An additional 4.60 ml of triethylamine were added. After 48 hours, the solvent was removed under reduced pressure and the residue was purified by chromatography on silica gel with ethyl acetate/petroleum ether (1:2). Crystallization from ethyl acetate gave 4.02 g of 3-[8-(acetoxymethyl)-6,7,8,9-tetrahydropyrido[1,2-a]indol-10-yl]-4-(1-methyl-3-indolyl)furan-2,5-dione of melting point 174°–178° C.

EXAMPLE 2

2.50 g of trifluoromethanesulfonic anhydride in 330 ml of dichloromethane were treated at 0° C. under a nitrogen atmosphere with a suspension of 1.87 g of the pyrroledione product of Example 1 and 0.94 g of collidine in 280 ml of dichloromethane. After 2.5 hours, the mixture was allowed to warm to 10° C. Then, 37 ml of 33% aqueous ammonia were added and the mixture was allowed to warm to room temperature overnight. The mixture was washed with water, dried and evaporated. The residue was subjected to chromatography on silica gel with dichloromethane/methanol/acetic acid/water (90:18:3:2). The combined product-containing fractions were treated with 2M hydrochloric acid and evaporated to give 930 mg of 3-[8-(aminomethyl)-6,7,8,9-tetrahydropyrido[1,2-a]indol-10-yl]-4-(1-methyl-3-indolyl)-1H-pyrrole-2,5-dione hydrochloride of melting point 310°–313° C.

EXAMPLE 3

265 mg of trifluoromethanesulfonic anhydride in 40 ml of dichloromethane were treated at 0° C. under a nitrogen atmosphere with a suspension of 200 mg of the pyrroledione product of Example 1 and 100 mg of collidine in 30 ml of dichloromethane. After 5 hours, 0.5 ml of a 33% solution of trimethylamine in ethanol was added and the mixture was stirred for 18 hours. The resulting precipitate was filtered off and dried to give 237 mg of 3-[6,7,8,9-tetrahydro-8-[(trimethylammonio)methyl]pyrido[1,2-a]indol-10-yl]-4-(1-methyl-3-indolyl)-1H-pyrrole-2,5-dione trifluoromethanesulfonate of melting point 320°–324° C.

EXAMPLE 4

265 mg of trifluoromethanesulfonic anhydride in 40 ml of dichloromethane were treated at 0° C. under a nitrogen atmosphere with a suspension of 200 mg of the pyrroledione product of Example 1 and 100 mg of collidine in 30 ml of dichloromethane. After 5 hours, 0.75 ml of a 33% solution of methylamine in methylated spirit was added and the mixture was stirred for 18 hours. An additional 0.5 ml of the aforementioned methylamine solution was then added. After 4 hours, the solvent was removed by evaporation and the precipitate was filtered off and purified by chromatography on silica gel with dichloromethane/methanol/acetic acid/water (90:18:3:2). The solid product was stirred with ethyl acetate saturated with hydrogen chloride for 2 hours. The resulting solid was filtered off and dried to give 55 mg of 3-[6,7,8,9-tetrahydro-8-[(methylamino)methyl]pyrido[1,2-a]indol-10-yl]-4-(1-methyl-3-indolyl)-1H-pyrrole-2,5-dione hydrochloride of melting point 337°–340° C.

EXAMPLE 5

185 mg of trifluoromethanesulfonic anhydride in 30 ml of dichloromethane were treated at 0° C. under a nitrogen atmosphere with a suspension of 140 mg of the pyrroledione product of Example 1 and 70 mg of collidine in 25 ml of dichloromethane. After 1.5 hour, 0.8 ml of a 33% solution of dimethylamine in ethanol was added and the mixture was stirred for 2.5 hours. The solvent was removed under reduced pressure and the residue was triturated with methanol to give a solid which was stirred with ethyl acetate saturated with hydrogen chloride. The solid was filtered off and dried to give 70 mg of 3-[6,7,8,9-tetrahydro-8-[(dimethylamino)methyl]pyrido[1,2-a]indol-10-yl]-4-(1-methyl-3-indolyl)-1H-pyrrole-2,5-dione hydrochloride of melting point 335°–336° C.

EXAMPLE 6

A solution of 170 mg of the pyrroledione product of Example 1 in 55 ml of dichloromethane was treated with 87 mg of methanesulfonic anhydride and 1 ml of pyridine. The resulting solution was stirred under nitrogen for 1 hour. An additional 30 mg of methanesulfonic anhydride were then added. After 1 hour, the mixture was washed with water, dried and evaporated. Crystallization of the residue from ethyl acetate/n-hexane gave 150 mg of 3-[6,7,8,9-tetrahydro-8-(methylsulphonyloxymethyl)pyrido[1,2-a]indol-10-yl]-4-(1-methyl-3-indolyl)-1H-pyrrole-2,5-dione of melting point 259°–261° C.

EXAMPLE 7

A solution of 120 mg of the pyrroledione product of Example 6 in 6 ml of dimethylformamide and 6 ml of 33% aqueous ammonia was heated to 140° C. for 6 hours. The cooled mixture was poured into water and the precipitate was filtered off. The product was purified by chromatography on silica gel with dichloromethane/acetic acid/methanol/water (60:18:2:3). Trituration with ethyl acetate gave 50 mg of 3-[8-(formamidomethyl)-6,7,8,9-tetrahydropyrido[1,2-a]indol-10-yl]-4-(1-methyl-3-indolyl)-1H-pyrrole-2,5-dione of melting point 332°–334° C.

EXAMPLE 8

A solution of 100 mg of the pyrroledione product of Example 6 and 75 mg of thiourea in 5 ml of dimethylformamide was heated to 80° C. under a nitrogen atmosphere for 18 hours. The solvent was removed by evaporation and the residue was purified by chromatography on silica gel with dichloromethane/methanol/acetic acid/water (90:18:3:2). The residue was triturated with ethyl acetate to give 80 mg of 3-[8-[(amidinothio)methyl]-6,7,8,9-tetrahydropyrido[1,2-a]-indol-10-yl]-4-(1-methyl-3-indolyl)-1H-pyrrole-2,5-dione methanesulfonate of melting point 200°–205° C.

EXAMPLE 9

In a manner analogous to that described in the first paragraph of Example 1, from 3-[7-(acetoxymethyl)-6,7,8,9-tetrahydropyrido[1,2-a]indol-10-yl]-4-(1-methyl-3-indolyl)furan-2,5-dione, there was prepared 3-[6,7,8,9-tetrahydro-7-(hydroxymethyl)pyrido[1,2-a]indol-10-yl]-4-(1-methyl-3-indolyl)-1H-pyrrole-2,5-dione of melting point 239°–242° C.

The furandione starting material was prepared as follows:

a) 6.6 ml of a 1.6M solution of n-butyllithium in n-hexane were added to a stirred solution of 1.11 g of diisopropylamine in 150 ml of tetrahydrofuran at –78° C. under nitrogen. The mixture was allowed to warm to –20° C. for 5 minutes and was then again cooled to –78° C. Then, 1.85 g of 6,7,8,9-tetrahydropyrido[1,2-a]indol-6-one in 10 ml of tetrahydrofuran were added dropwise. After stirring at –78° C. for 0.5 hour, 1.19 g of ethyl chloroformate were added and the mixture was allowed to warm to room temperature. The solvent was removed by evaporation and the residue was partitioned between diethyl ether and 2M hydrochloric acid. The ethereal extracts were washed with saturated sodium bicarbonate solution, dried and concentrated to give an oil. This oil was purified by chromatography on silica gel with dichloromethane. Crystallization of the product from methanol gave 1.35 g of ethyl 6,7,8,9-tetrahydro-6-oxopyrido[1,2-a]indole-7-carboxylate of melting point 82°–84° C.

b) 30 ml of a 1M solution of borane in tetrahydrofuran were added to a stirred solution of 1.25 g of the carboxylate of a) and the resulting solution was heated to reflux for 2 hours under a nitrogen atmosphere. Thereafter, 6 spoon spatula measures of silica gel were added to the cooled solution and the solvent was removed by evaporation. The residue was purified by chromatography on silica gel with ethyl acetate/n-hexane (1:1) to give an oil. This oil was dissolved in 60 ml of dichloromethane containing 8 ml of pyridine and 2 ml of acetic anhydride. After 18 hours, the solution was washed with 60 ml of 2M hydrochloric acid and 20 ml of saturated sodium bicarbonate solution, dried and evaporated to give an oil. A solution of this oil in 60 ml of diethyl ether was treated with 630 mg oxalyl chloride under a nitrogen atmosphere. The solvent was removed under reduced pressure and the residue was dissolved in 100 ml of dichloromethane. Then, 920 mg of 1-methyl-3-indolylacetic acid and 975 mg of triethylamine were added to this solution. After 72 hours, the solvent was removed by evaporation and the residue was purified by chromatography on silica gel with ethyl acetate/n-hexane (1:1). Crystallization from ethyl acetate gave 390 mg of 3-[7-(acetoxymethyl)-6,7,8,9-tetrahydropyrido[1,2-a]indol-10-yl]-4-(1-methyl-3-indolyl)furan-2,5-dione of melting point 190°–193° C.

EXAMPLE 10

200 mg of trifluoromethanesulfonic anhydride in 50 ml of dichloromethane were treated at 0° C. under a nitrogen atmosphere with a suspension of 150 mg of the pyrroledione product of Example 9 and 75 mg of collidine in 50 ml of dichloromethane. After 2 hours, 4 ml of 33% aqueous ammonia were added and the mixture was left to warm to room temperature overnight. The mixture was washed with water, dried and evaporated to dryness. The residue was purified by chromatography on silica gel with dichloromethane/methanol/acetone/water (90:18:3:2). Crystallization from dichloromethane/n-hexane gave 85 mg of 3-[7-(aminomethyl)-6,7,8,9-tetrahydropyrido[1,2-a]indol-10-yl]-4-(1-methyl-3-indolyl)-1H-pyrrole-2,5-dione of melting point 160°–165° C.

EXAMPLE 11

A Solution of 120 mg of the pyrroledione product of Example 9 in 80 ml of dichloromethane was treated with 2 ml of pyridine and 100 mg of methanesulfonic anhydride under a nitrogen atmosphere. After stirring for 18 hours, the mixture was washed with 2M hydrochloric acid and saturated sodium bicarbonate solution, dried and evaporated to give 130 mg of a gum. This gum was dissolved in 40 ml of ethanol containing 200 mg of thiourea and the mixture was heated to reflux for 72 hours. The solvent was removed by evaporation and the residue was purified by chromatography on silica gel with dichloromethane/methanol/acetone/water (90:18:3:2). Crystallization from methanol/dichloromethane gave 30 mg of 3-[7-(amidinothiomethyl)-6,7,8,9-tetrahydropyrido[1,2-a]indol-10-yl]-4-(1-methyl-3-indolyl)-1H-pyrrole-2,5-dione methanesulfonate of melting point 195°–198° C.

EXAMPLE 12

A solution of 72 mg of 3-(6,7,8,9-tetrahydropyrido[1,2-a]indol-10-yl)-4-(1-methyl-3-indolyl)furan-2,5-dione in 5 ml of dimethylformamide and 5 ml of 33% aqueous ammonia was heated to 140° C. for 4 hours. The resulting crystals were filtered off and dried to give 50 mg of 3-(6,7,8,9-tetrahydro-pyrido[1,2-a]indol-10-yl)-4-(1-methyl-3-indolyl)-1H-pyrrole-2,5-dione of melting point 286°–289° C.

The furandione starting material was prepared as follows:

a) A solution of 1.03 g of ethyl 6,7-dihydro-9-hydroxypyrido[1,2-a]indole-8-carboxylate in 20 ml of ethanol, 10 ml of water and 10 ml of concentrated hydrochloric acid was heated at 80° C. for 3 hours. The solvents were evaporated to give 740 mg of 7,8-dihydropyrido[1,2-a]indol-9(6H)-one of melting point 138°–140° C.

b) A solution of 740 mg of the product of a), 600 mg of hydrazine hydrate and 440 mg of potassium hydroxide in 2 ml of ethanol and 4 ml of diethylene glycol was heated at 100° C. under reflux for 1.5 hours. The mixture was heated at 180° C. for 2 hours. Then, 50 ml of dichloromethane were added and the organic phase was washed with 2M hydrochloric acid and water. The solvent was removed by evaporation to give 405 mg of 6,7,8,9-tetrahydropyrido-[1,2-a]indole.

c) 350 mg of oxalyl chloride were added dropwise to a solution of 450 mg of the product of b) in 13 ml of dichloromethane at 0° C. After stirring for 2 hours, the solvent was removed by evaporation and the residue was dissolved in dichloromethane. Then, 497 mg of 1-methyl-3-indolylacetic acid and 0.73 ml of triethylamine were added to this solution and the mixture was stirred at room temperature for 60 hours. The solvent was evaporate and the residue was purified by chromatography on silica gel with dichloromethane. Trituration of the product with ethyl acetate gave 100 mg of 3-(6,7,8,9-tetrahydropyrido[1,2-a]indol-10-yl)-4-(1-methyl-3-indolyl)furan-2,5-dione in the form of a red solid of melting point 276°–278° C.

EXAMPLE 13

In a manner analogous to that described in the first paragraph of Example 1, from 3-[8-(2-acetoxyethyl)-6,7,8,9-tetrahydropyrido[1,2-a]indol-10-yl]-4-(1-methyl-3-indolyl)furan-2,5-dione there was prepared 3-[6,7,8,9-tetrahydro-8-(2-hydroxyethyl)pyrido[1,2-a]indol-10-yl]-4-(1-methyl-3-indolyl)-1H-pyrrole-2,5-dione of melting point 261°–263° C.

The furandione starting material was prepared as follows:

a) A solution of 6.52 g of 8-(2-acetoxyethyl)-6,7,8,9-tetrahydro-9-oxopyrido[1,2-a]indole in 48 ml of dichloromethane was treated with 2.5 ml of ethanedithiol and 3.13 ml of titanium tetrachloride. The resulting solution was heated at reflux under nitrogen for 18 hours. An additional 4 ml of ethanedithiol and 9 ml of titanium tetrachloride were added and heating was continued for 4.5 hours. The mixture was washed with water, dried and evaporated. The residue was purified by chromatography on silica gel with ethyl acetate/petroleum ether (1:3) to give 7.7 g of 8'-(2-acetoxyethyl)-7',8'-dihydrospiro[1,3-dithiolane-2',9'(6'H)-pyrido[1,2-a]indole].

b) A solution of 5 g of the product of a) in 200 ml of ethanol was shaken with 8 spoon spatula measures of Raney nickel for 3.5 hours. The mixture was filtered and the filter residue was washed with ethanol. The combined filtrate and washings were evaporated to dryness and the residue was purified by chromatography on silica gel with ethyl acetate/petroleum ether (1:2) to give 620 mg of 8-(2-acetoxyethyl)-6,7,8,9-tetrahydropyrido[1,2-a]indole.

c) 1.19 g of oxalyl chloride were added dropwise to a solution of 2.29 g of the product of b) in 50 ml of diethyl ether at 0° C. After 2.5 hours, the solvent was removed by evaporation and the residue was dissolved in dichloromethane. Then, 1.68 g of 1-methyl-3-indolylacetic acid and 2.45 ml of triethylamine were added to this solution and the mixture was heated to reflux under nitrogen for 18 hours. The solvent was evaporated and the residue was purified by chromatography on silica gel with ethyl acetate/petroleum ether (1:2). Crystallization from ethyl acetate gave 625 mg of 3-[8-(2-acetoxyethyl)-6,7,8,9-tetrahydropyrido[1,2-a]indol-10-yl]-4-(1-methyl-3-indolyl)-furan-2,5-dione of melting point 159°–161° C.

EXAMPLE 14

A solution of 115 mg of 3-[8-(2-acetoxyethyl)-6,7,8,9-tetrahydropyrido[1,2-a]indol-10-yl]-4-(1-methyl-3-indolyl)furan-2,5-dione in 1 ml of dimethylformamide and 2 ml of 33% aqueous ammonia was heated to 140° C. for 4 hours. The cooled mixture was evaporated and the residue was purified by chromatography on silica gel with ethyl acetate/petroleum ether (2:1). Crystallization from ethyl acetate/petroleum ether gave 13 mg of 3-[8-(2-acetoxyethyl)-6,7,8,9-tetrahydropyrido[1,2-a]indol-10-yl]-4-(1-methyl-3-indolyl)-1H-pyrrole-2,5-dione of melting point 272°–274° C.

EXAMPLE 15

A solution of 500 mg of the pyrroledione product of Example 13 in 50 ml of dichloromethane was treated with 218 mg of methanesulfonic anhydride and 1 ml of pyridine. The resulting solution was stirred at room temperature under a nitrogen atmosphere for 1 hour. An additional 20 mg of methanesulfonic anhydride were then added and stirring was continued for 0.5 hour. The mixture was washed with water, dried and evaporated. Crystallization of the residue from ethyl acetate/petroleum ether gave 540 mg of 3-[6,7,8,9-tetrahydro-8-(2-methylsulfonyloxyethyl)pyrido-[1,2-a]indol-10-yl]-4-(1-methyl-3-indolyl)-1H-pyrrole-2,5-dione of melting point 244°–245° C.

EXAMPLE 16

A solution of 500 mg of the pyrroledione product of Example 15 and 250 mg of sodium azide in 10 ml of dimethylformamide was heated at 70° C. for 3 hours. The solvent was removed by evaporation and the solid was partitioned between ethyl acetate and water. The insoluble material was filtered off and dried to give 425 mg of 3-[8-(2-azidoethyl)-6,7,8,9-tetrahydropyrido[1,2-a]indol-10-yl]-4-(1-methyl-3-indolyl)-1H-pyrrole-2,5-dione of melting point 262°–264° C.

EXAMPLE 17

200 mg of the pyrroledione product of Example 16 in 70 ml of methanol containing 40 mg of 10% Pd/C were shaken under a hydrogen atmosphere at a pressure of 3 atmospheres for 48 hours. The supernatant was decanted and evaporated. The residue was treated with 50 ml of a saturated solution of hydrogen chloride in ethyl acetate and was then purified by chromatography on silica gel with dichloromethane/methanol/acetic acid/water (60:18:2:3). Crystallization from ethyl acetate gave 20 mg of 3-[8-(2-aminoethyl)-6,7,8,9-tetrahydropyrido[1,2-a]indol-10-yl]-4-(1-methyl-3-indolyl)-1H-pyrrole-2,5-dione of melting point 160°–165° C.

EXAMPLE 18

In a manner analogous to that described in the first paragraph of Example 12, from 3-[2,3-dihydro-1H-pyrrolo[1,2-a]indol-9-yl]-4-(1-methyl-3-indolyl)furan-2,5-dione there was obtained 3-[2,3-dihydro-1H-pyrrolo[1,2-a]indol-9-yl]-4-(1-methyl-3-indolyl)-1H-pyrrole-2,5-dione of melting point 260°–270° C.

The furandione starting material was prepared as follows:

175 mg of oxalyl chloride were added dropwise to a solution of 200 mg of 2,3-dihydro-1H-pyrrolo[1,2-a]indole in 7 ml of diethyl ether at 0° C. under a nitrogen atmosphere. After 1 hour, the solvent was removed under reduced pressure and the residue was dissolved in 14 ml of dichloromethane. 245 mg of 1-methyl-3-indolylacetic acid and 265 mg of triethylamine were added to this solution and the mixture was stirred at room temperature for 72 hours. The solvent was removed under reduced pressure and the residue was purified by chromatography on silica gel with ethyl acetate/petroleum ether (1:2). Crystallization from ethyl acetate gave 70 mg of 3-[2,3-dihydro-1H-pyrrolo[1,2-a]indol-9-yl]-4-(1-methyl-3-indolyl)furan-2,5-dione of melting point 125°–130° C.

EXAMPLE 19

In a manner analogous to that described in the first paragraph of Example 1, from 3-[2-(acetoxymethyl)-2,3-dihydro-1H-pyrrolo[1,2-a]indol-9-yl]-4-(1-methyl-3-indolyl)furan-2,5-dione, there was prepared 3-[2,3-dihydro-2-(hydroxymethyl)-1H-pyrrolo[1,2-a]indol-9-yl]-4-(1-methyl-3-indolyl)-1H-pyrrole-2,5-dione of melting point 238°–240° C.

The furandione starting material was prepared as follows:

a) 6 spoon spatula measures of Raney nickel were added to a solution of 5.08 g of ethyl 2,3-dihydro-1-oxo-1H-pyrrolo[1,2-a]indole-2-carboxylate in 180 ml of ethanol and 90 ml of water. The mixture was heated to reflux for 10 hours. Then, an additional 3 spoon spatula measures of Raney nickel were added. Heating was continued for 5.5 hours, whereupon the mixture was cooled and filtered. The filter residue was washed with ethyl acetate and dichloromethane. The combined filtrate and washings were evaporated and the residue was purified by chromatography on silica gel with diethyl ether/petroleum ether (1:2). Crystallization from methanol gave 635 mg of ethyl 2,3-dihydro-1H-pyrrolo[1,2-a]indole-2-carboxylate of melting point 55°–57° C.

b) 4 ml of a 1M solution of lithium aluminum hydride in tetrahydrofuran were added to a solution of 750 mg of ethyl 2,3-dihydro-1H-pyrrolo[1,2-a]indole-2-carboxylate in 30 ml of tetrahydrofuran. After 1 hour, 30 ml of saturated ammonium chloride solution were added and the mixture was evaporated. The residue was extracted with dichloromethane and the organic extract was dried and evaporated. Crystallization of the residue from diethyl ether/petroleum ether gave 355 mg of 2,3-dihydro-2-(hydroxymethyl)-1H-pyrrolo[1,2-a]indole of melting point 76°–78° C.

c) A solution of 355 mg of the product of b) in 20 ml of dichloromethane containing 2 ml of acetic anhydride and 2 ml of pyridine was stirred for 2 hours. The solvents were evaporated and the residue was partitioned between dichloromethane and water. The organic phase was dried and evaporated to give 420 mg of 2-(acetoxymethyl)-2,3-dihydro-1H-pyrrolo[1,2-a]indole.

d) 290 mg of oxalyl chloride were added dropwise to a solution of 420 mg of the product of c) in 14 ml of diethyl ether under a nitrogen atmosphere. After 1 hour, the solvent was removed under reduced pressure and the residue was dissolved in dichloromethane. Then, 420 mg of 1-methyl-3-indolylacetic acid and 485 mg of triethylamine were added to this solution and the mixture was stirred for 72 hours. The solvent was evaporated and the residue was purified by chromatography on silica gel with ethyl acetate/petroleum ether (1:1). Crystallization from ethyl acetate gave 90 mg of 3-[2-(acetoxymethyl)-2,3-dihydro-1H-pyrrolo[1,2-a]indol-9-yl]-4-(1-methyl-3-indolyl)furan-2,5-dione of melting point 208°–211° C.

EXAMPLE 20

A solution of 150 mg of 3-[2-t-butoxycarbonyl-1,2,3,4-tetrahydropyrazino[1,2-a]indol-10-yl]-4-(1-methyl-3-indolyl)furan-2,5-dione in 4 ml of dimethylformamide and 8 ml of 33% aqueous ammonia was heated to 140° C. for 4 hours. The mixture was extracted with ethyl acetate and the organic extract was washed with water, dried and evaporated to give a gum. Purification was effected by chromatography on silica gel with dichloromethane/methanol/acetic acid/water. The resulting imide was dissolved in 30 ml of ethanol and 5 ml of 2M hydrochloric acid and the resulting solution was heated to reflux for 2 hours. Removal of the solvent by evaporation and trituration of the residue with ethyl acetate gave 35 mg of 3-[1,2,3,4-tetrahydropyrazino-[1,2-a]indol-10-yl]-4-(1-methyl-3-indolyl)-1H-pyrrole-2,5-dione hydrochloride of melting point 268°–270° C.

The furandione starting material was prepared as follows:

a) A solution of 450 mg of 1,2,3,4-tetrahydropyrazino[1,2-a]indole in 30 ml of dichloromethane was treated at 0° C. under a nitrogen atmosphere with 303 mg of triethylamine and 615 mg of di(t-butyl) dicarbonate. The mixture was stirred at 0° C. for 4 hours and then washed with saturated sodium bicarbonate solution, dried and evaporated to give an oil. Crystallization from methanol gave 580 mg of t-butyl 1,2,3,4-tetrahydropyrazino[1,2-a]indole-2-carboxylate of melting point 103°–105° C.

b) 230 mg of oxalyl chloride were added dropwise to a stirred solution of 450 mg of the product of a) in 30 ml of diethyl ether at 0° C. After stirring, the solution was evaporated and the residue was dissolved in 50 ml of dichloromethane. 360 mg of 1-methyl-3-indolylacetic acid and 350 mg of triethylamine were added and the mixture was stirred for 90 hours. The solvent was evaporated and the residue was purified by chromatography on silica gel with ethyl acetate/petroleum ether (2:3) to give 180 mg of a gum. A sample was crystallized from ethyl acetate/n-hexane to give 3-[2-t-butoxycarbonyl-1,2,3,4-tetrahydropyrazino[1,2-

EXAMPLE 21

In a manner analogous to that described in the first paragraph of Example 12, from 3-(5,6-dihydro-4H-pyrrolo[3,2,1-ij]quinolin-1-yl)-4-(1-methyl-3-indolyl)furan-2,5-dione there was prepared 3-(5,6-dihydro-4H-pyrrolo-[3,2,1-ij]quinolin-1-yl)-4-(1-methyl-3-indolyl)-1H-pyrrole-2,5-dione of melting point 285°–288° C.

The furandione starting material was prepared as follows:

1.22 g of oxalyl chloride were added dropwise to a solution of 1.5 g of 5,6-dihydro-4H-pyrrolo[3,2,1-ij]quinoline in 60 ml of dichloromethane under a nitrogen atmosphere. After 1 hour, the solvent was removed under reduced pressure and the residue was dissolved in 120 ml of dichloromethane. 1.9 g of 1-methyl-3-indolylacetic acid and 2.02 g of triethylamine were added to this solution and the mixture was stirred for 18 hours. The solvent was removed under reduced pressure and the residue was purified by chromatography on silica gel with ethyl acetate/petroleum ether (1:2). Further purification by chromatography was effected with dichloromethane. Crystallization from ethyl acetate gave 690 mg of 3-(5,6-dihydro-4H-pyrrolo[3,2,1-ij]quinolin-1-yl)-4-(1-methyl-3-indolyl)furan-2,5-dione of melting point 217°–219° C.

EXAMPLE 22

In a manner analogous to that described in the first paragraph of Example 1, from 3-[5-(acetoxymethyl)-5,6-dihydro-4H-pyrrolo[3,2,1-ij]quinolin-1-yl]-4-(1-methyl-3-indolyl)furan-2,5-dione, there was prepared 3-[5,6-dihydro-5-(hydroxymethyl)-4H-pyrrolo[3,2,1-ij]quinolin-1-yl]-4-(1-methyl-3-indolyl)-1H-pyrrole-2,5-dione of melting point 223°–225° C.

The furandione starting material was prepared as follows:

a) 33.4 ml of a 1.6M solution of n-butyllithium in hexane were added to a solution of 8.13 ml of diisopropylamine in 420 ml of tetrahydrofuran at −78° C. under a nitrogen atmosphere. After 0.5 hour, 4.6 g of 1,2,5,6-tetrahydro-4-oxo-4H-pyrrolo-[3,2,1-ij]quinoline were added and the mixture was stirred at −78° C. for 0.5 hour. Then, 2.77 ml of ethyl chloroformate were added and stirring was continued for 1 hour. The reaction was quenched with water and the mixture was evaporated. The residue was purified by chromatography on silica gel with ethyl acetate/petroleum ether (1:2). Crystallization from diethyl ether gave 2.8 g of ethyl 1,2,5,6-tetrahydro-4-oxo-4H-pyrrolo[3,a,1-ij]quinoline-5-carboxylate of melting point 88°–90° C.

b) 15 ml of a 1M solution of borane in tetrahydrofuran were added to a solution of 2.8 g of the product of a) in 100 ml of tetrahydrofuran and the resulting solution was heated to reflux for 2 hours. An additional 55 ml of borane were added and heating was continued for 12 hours. The solvent was removed under reduced pressure, water and 2M hydrochloric acid were added and the mixture was extracted with dichloromethane. The solvent was evaporated and the residue was dissolved in diethyl ether. The solution obtained was treated with 12 ml of a 1M solution of lithium aluminum hydride in diethyl ether and the mixture was stirred under a nitrogen atmosphere for 18 hours. Water was added and the mixture was extracted with dichloromethane. Removal of the solvent under reduced pressure gave 1.4 g of 1,2,5,6-tetrahydro-4H-pyrrolo[3,2,1-ij]quinoline-5-methanol.

c) A solution of 1.4 g of the product of b) in 50 ml of dichloromethane was treated with 4 ml of acetic anhydride and 2 ml of pyridine. After 4 hours, an additional 4 ml of acetic anhydride were added and the mixture was stirred for 18 hours. The solvent was removed under reduced pressure and the residue was partitioned between water and dichloromethane. The organic phase was evaporated and the residue was dissolved in toluene and heated to reflux in the presence of 250 mg of 10% palladium/carbon for 18 hours. An additional 250 mg of 10% palladium/carbon were then added and heating was continued for an additional 20 hours. The mixture was filtered and the filtrate was evaporated. The residue obtained was purified by chromatography on silica gel with ethyl acetate/petroleum ether (1:2) to give 350 mg of 5-(acetoxymethyl)-5,6-dihydro-4H-pyrrolo[3,2,1-ij]quinoline.

d) 315 mg of oxalyl chloride were added to a solution of 570 mg of the product of c) in 15 ml of dichloromethane under a nitrogen atmosphere. The solvent was removed under reduced pressure and the residue was dissolved in dichloromethane. Then, 472 mg of 1-methyl-3-indolylacetic acid and 505 mg of triethylamine were added and the mixture was stirred for 72 hours. The solvent was removed under reduced pressure and the residue was purified by chromatography on silica gel with dichloromethane. Crystallization from ethyl acetate/n-hexane gave 140 mg of 3-[5-(acetoxymethyl)-5,6-dihydro-4H-pyrrolo[3,2,1-ij]quinolin-1-yl]-4-(1-methyl-3-indolyl)furan-2,5-dione of melting point 198°–200° C.

EXAMPLE 23

In a manner analogous to that described in Example 11, from the pyrroledione product of Example 22, there was prepared 3-[5-(amidinothiomethyl)-5,6-dihydro-4H-pyrrolo[3,2,1-ij]quinolin-1-yl]-4-(1-methyl-3-indolyl)-1H-pyrrole-2,5-dione methanesulfonate of melting point 190°–195° C.

EXAMPLE 24

In a manner analogous to that described in Example 2, from the pyrroledione product of Example 22, there was prepared 3-[5-(aminomethyl)-5,6-dihydro-4H-pyrrolo[3,2,1-ij]quinolin-1-yl]-4-(1-methyl-3-indolyl)-1H-pyrrole-2,5-dione hydrochloride of melting point 248°–250° C.

EXAMPLE 25

In a manner analogous to that described in the first paragraph of Example 1, from 3-[8-(acetoxymethyl)-6,7,8,9-tetrahydropyrido[1,2-a]indol-10-yl]-4-phenylfuran-2,5-dione (obtained as described in the last paragraph of Example 1 by using phenylacetic acid in place of 1-methyl-3-indolylacetic acid), there was prepared 3-[6,7,8,9-tetrahydro-8-(hydroxymethyl)pyrido[1,2-a]indol-10-yl]-4-phenyl-1H-pyrrole-2,5-dione of melting point 276°–278° C.

EXAMPLE 26

In a manner analogous to that described in the first paragraph of Example 1, from 4-[8-(acetoxymethyl)-6,7,8,9-tetrahydropyrido[1,2-a]indol-10-yl]-3-(3-benzo[b]thienyl)furan-2,5-dione (obtained as described in the last paragraph of Example 1 by using 3-benzo[b]thienylacetic acid in place of 1-methyl-3-indolylacetic acid), there was prepared 3-(3-benzo[b]thienyl)-4-[6,7,8,9-tetrahydro-8-(hydroxymethyl)pyrido[1,2-a]indol-10-yl]-1H-pyrrole-2,5-dione of melting point 226°–227° C.

EXAMPLE 27

In a manner analogous to that described in the first paragraph of Example 1, from 3-[8-(acetoxymethyl)-6,7,8, 9-tetrahydropyrido[1,2-a]indol-10-yl]-4-(1-naphthyl)furan-2,5-dione (obtained as described in the last paragraph of Example 1 by using 1-naphthylacetic acid in place of 1-methyl-3-indolylacetic acid), there was prepared 3-[6,7,8,9-tetrahydro-8-(hydroxymethyl)pyrido[1,2-a]indol-10-yl]-4-(1-naphthyl)-1H-pyrrole-2,5-dione of melting point 221°–222° C.

EXAMPLE 28

In a manner analogous to that described in Example 10, from the pyrroledione product of Example 19, there was prepared 3-[2-(aminomethyl)-2,3-dihydro-1H-pyrrolo[1,2-a]indol-9-yl]-4-(1-methyl-3-indolyl)-1H-pyrrole-2,5-dione of melting point 208°–211° C.

EXAMPLE 29

In an analogous manner to that described in Example 10, from the pyrroledione product of Example 25, there was prepared 3-[8-(aminomethyl)-6,7,8,9-tetrahydropyrido[1,2-a]indol-10-yl]-4-phenyl-1H-pyrrole-2,5-dione of melting point 249°–250° C.

EXAMPLE 30

A suspension of 100 mg of the pyrroledione product of Example 20 in 10 ml of dichloromethane was treated under nitrogen with 0.08 ml of triethylamine and 86 mg of phenyl chloroformate. The mixture was stirred for 2 hours and then the solvent was evaporated. Chromatography of the residue on silica gel with ethyl acetate/n-hexane (1:1) gave a gum which was dissolved in a mixture of 5 ml of isopropanol and 10 ml of 33% aqueous ammonia. The mixture was diluted with water and extracted with dichloromethane. The combined dichloromethane extracts were dried and evaporated. Crystallization of the residue from ethyl acetate/n-hexane gave 45 mg of 3-[1,2,3,4-tetrahydro-2-(phenoxycarbonyl)pyrazino[1,2-a]indol-10-yl]-4-(1-methyl-3-indolyl)-1H-pyrrole-2,5-dione of melting point 160°–165° C.

EXAMPLE 31 a) A solution of 80 mg of the pyrroledione product of Example 20 in 20 ml of dichloromethane was treated with 10 ml of 5% aqueous sodium hydrogen carbonate. The stirred mixture was treated with a solution of 125 mg of trifluoroacetamidoacetyl chloride in 5 ml of dichloromethane. After 17 hours, the phases were separated and the organic phase was dried and evaporated. Chromatography of the residue on silica gel with ethyl acetate/n-hexane (2:1) and crystallization from ethyl acetate/n-hexane gave 70 mg of 3-[2-[(trifluoroacetamido)acetyl]-1,2,3,4-tetrahydropyrazino[1,2-a]indol-10-yl]-4-(1-methyl-3-indolyl)-1H-pyrrole-2,5-dione of melting point 170°–172° C.

b) A solution of 65 mg of the product of a) in 10 ml of methanol was treated with 5 ml of 33% aqueous ammonia. After 4 hours, the solvent was removed by evaporation and the residue was partitioned between dichloromethane and water. The organic phase was washed with water, dried and evaporated. Chromatography of the residue on silica gel with chloroform/methanol/acetic acid/water (60:18:2:3) gave a gum which was dissolved in glacial acetic acid and treated with 20 ml of 1M hydrochloric acid. Evaporation of the solvent and trituration of the residue with diethyl ether gave 35 mg of 3-[2-(aminoacetyl)-1,2,3,4-tetrahydropyrazino[1,2-a]indol-10-yl]-4-(1-methyl-3-indolyl)-1H-pyrrole-2,5-dione hydrochloride of melting point 235° C. (decomposition).

EXAMPLE 32 a) A solution of 100 mg of the pyrroledione product of Example 20 in 40 ml of dichloromethane was treated under a nitrogen atmosphere with 125 mg of 1,1-carbonyldiimidazole and the mixture was stirred for 24 hours. The solution was washed with water, dried and evaporated. Trituration of the residue with ethyl acetate gave 84 mg of 3-[1,2,3,4-tetrahydro-2-(1-imidazolylcarbonyl)pyrazino[1,2-a]indol-10-yl]-4-(1-methyl-3-indolyl)-1H-pyrrole-2,5-dione of melting point 295° C. (decomposition).

b) 80 mg of the product of a) were dissolved in a mixture of 20 ml of dimethylformamide and 20 ml of 33% aqueous ammonia. The mixture was stirred for 17 hours and the solvent was evaporated. Chromatography of the residue on silica gel with methanol/ethyl acetate (1:9) gave a solid which was crystallized from methanol. There were obtained 45 mg of 3-[2-carbamoyl-1,2,3,4-tetrahydropyrazino[1,2-a]indol-10-yl]-4-(1-methyl-3-indolyl)-1H-pyrrole-2,5-dione of melting point 295° C. (decomposition).

EXAMPLE 33

A solution of 505 mg of the pyrroledione product of Example 2 in 20 ml of dimethylformamide was treated with a solution of 222 mg of 1,1-thiocarbonyldiimidazole in 5 ml of tetrahydrofuran. After 17 hours the solvent was evaporated and the residue was purified by chromatography on silica gel with methanol/dichloromethane (1:99). Trituration with n-hexane gave 297 mg of 3-[6,7,8,9-tetrahydro-8-isothiocyanato-pyrido[1,2-a]indol-10-yl]-4-(1-methyl-3-indolyl)-1H-pyrrole-2,5-dione in the form of a red solid of melting point 285°–287° C.

EXAMPLE 34

250 mg of the pyrroledione product of Example 2 were stirred in a mixture of 25 ml of dichloromethane and 15 ml of 5% aqueous sodium hydrogen carbonate. The mixture was treated with 1 ml of benzoyl chloride and stirred for 17 hours. The phases were separated and the organic phase was dried and evaporated. Chromatography of the residue on silica gel with methanol/dichloromethane (7:93) followed by trituration with n-hexane gave 220 mg of 3-[8-(benzamidomethyl)-6,7,8,9-tetrahydropyrido[1,2-a]indol-10-yl]-4-(1-methyl-3-indolyl)-1H-pyrrole-2,5-dione of melting point 297°–303° C.

EXAMPLE 35

A solution of 150 mg of 3-[7-acetoxy-6,7,8,9-tetrahydropyrido[1,2-a]indol-10-yl]-4-(1-methyl-3-indolyl)furan-2,5-dione in 6 ml of dimethylformamide and 6 ml of 33% aqueous ammonia was heated to 150° C. for 6 hours. The mixture was extracted with ethyl acetate and the organic extracts were washed with water, dried and evaporated. Crystallization of the residue from ethyl acetate gave 120 mg of 3-[6,7,8,9-tetrahydro-7-hydroxypyrido[1,2-a]indol-10-yl]-4-(1-methyl-3-indolyl)-1H-pyrrole-2,5-dione of melting point 252°–255° C.

The furandione starting material was prepared as follows:

a) A solution of 14.0 g of indole-2-methanol in 500 ml of dichloromethane was stirred with 76.4 g of activated manganese-IV oxide. After 1 hour, the solid was filtered off and washed with dichloromethane. The combined washings were concentrated and 33 g of (carbethoxymethylene)triphenylphosphorane were added. The resulting solution was heated to reflux under a nitrogen atmosphere. The solvent was evaporated to give an oil which was purified by chromatography on silica gel with ethyl acetate/n-hexane (1:3). The product was obtained as a 20:1 mixture of E/Z isomers. Crystallization from methanol gave 11.3 g of ethyl (E)-2-indolyl-2-propenoate of melting point 120°–122° C.

b) A solution of 7.2 g of ethyl (E)-2-indolyl-2-propenoate in 120 ml of dimethylformamide was treated with 1.47 g of a 60% dispersion of sodium hydride in mineral oil. The resulting solution was cooled to 0° C. and 7.17 g of t-butyl bromoacetate were added under an atmosphere of nitrogen. After 2 hours, the mixture was poured into 100 ml of 2M hydrochloric acid and extracted with ethyl acetate. The combined organic extracts were washed with water, dried and evaporated to give an oil. This oil was purified by chromatography on silica gel with diethyl ether/petroleum ether (1:3). Crystallization from diethyl ether/n-hexane gave 8.1 g of ethyl (E)-3-(1-t-butoxycarbonylmethyl)-2-indolyl]-2-propenoate of melting point 66°–68° C.

c) A solution of 8.0 g of the product of b) in 300 ml of ethanol was shaken with 800 mg of 10% palladium/carbon under a hydrogen atmosphere. The catalyst was filtered off and washed with ethyl acetate. The combined filtrate and washings were evaporated to give an oil which was dissolved in tetrahydrofuran. The solution was added to a solution of 2.8 g of potassium t-butoxide in tetrahydrofuran under a nitrogen atmosphere. Then the mixture was left to stir for 1 hour and the solvent was evaporated. The residue was partitioned between ethyl acetate and 2M hydrochloric acid. The organic phase was washed with water, dried and evaporated. The residue was purified by chromatography on silica gel with diethyl ether/n-hexane (1:4). There were obtained 4.55 g of t-butyl 6,7,8,9-tetrahydro-7-oxo-pyrido [1,2-a]indole-6-carboxylate.

d) A solution of 4.5 g of the product of c) in 200 ml of toluene was treated with four spoon spatula measures of silica gel and the mixture was heated to reflux for 3 hours under a nitrogen atmosphere. The solid was filtered off and washed with toluene. The combined filtrate and washings were evaporated to give a solid. Crystallization from diethyl ether/n-hexane gave 2.5 g of 8,9-dihydropyrido[1,2-a]indol-7(6H)-one of melting point 126°–128° C.

e) 190 mg of sodium borohydride were added to a stirred solution of 650 mg of 8,9-dihydropyrido[1,2-a]indol-7(6H)-one in 50 ml of methanol under a nitrogen atmosphere. The mixture was stirred and then poured into 100 ml of saturated ammonium chloride solution. The mixture was extracted with ethyl acetate and the combined extracts were dried and evaporated to give a solid. This was crystallized from diethyl ether/n-hexane and gave 500 mg of 6,7,8,9-tetrahydro-7-hydroxypyrido[1,2-a]indole of melting point 99°–100° C.

f) A solution of 500 mg of the product of e) in 5 ml of pyridine and 2 ml of acetic anhydride was stirred for 8 hours. The mixture was poured into 50 ml of 2M hydrochloric acid and extracted with ethyl acetate. The combined organic extracts were washed with 5% sodium bicarbonate solution and water, dried and evaporated to give 520 mg of an oil. A sample was crystallized from diethyl ether/n-hexane and there was obtained 7-acetoxy-6,7,8,9-tetrahydropyrido[1,2-a]indole of melting point 90°–95° C.

g) 320 mg of oxalyl chloride were added to a solution of 500 mg of the product of f) in 50 ml of diethyl ether under a nitrogen atmosphere. Then the solvent was removed under reduced pressure and the residue was dissolved in 50 ml of dichloromethane. 378 mg of 1-methyl-3-indolylacetic acid and 505 mg of triethylamine were added to this solution and the mixture was stirred for 72 hours. The solvent was removed under reduced pressure and the residue was purified by chromatography on silica gel with ethyl acetate/n-hexane (1:1). Crystallization from ethyl acetate gave 160 mg of 3-[7-acetoxy-6,7,8,9-tetrahydropyrido[1,2-a]indol-10-yl]-4-(1-methyl-3-indolyl)furan-2,5-dione of melting point 272°–275° C.

EXAMPLE 36

A solution of 85 mg of 3-[7-t-butoxyformamido-6,7,8,9-tetrahydropyrido[1,2-a]indol-10-yl]-4-(1-methyl-3-indolyl)furan-2,5-dione in 5 ml of dimethylformamide and 5 ml of 33% aqueous ammonia was heated to 100° C. for 1 hour. The cooled mixture was partitioned between ethyl acetate and water. The organic phase was washed with water, dried and evaporated. Crystallization from ethyl acetate/n-hexane gave 70 mg of 3-[7-t-butoxyformamido-6,7,8,9-tetrahydropyrido[1,2-a]indol-10-yl]-4-(1-methyl-3-indolyl)-1H-pyrrole-2,5-dione of melting point 159°–163° C.

The furandione starting material was prepared as follows:

a) A suspension of 555 mg of 8,9-dihydropyrido[1,2-a]indol-7(6H)-one and 4.62 g of ammonium acetate in 15 ml of methanol was treated with 250 mg of sodium cyanoborohydride. The mixture was stirred and then partitioned between ethyl acetate and water. The organic phase was dried and the solvent was removed under reduced pressure. The residual oil was subjected to chromatography on silica gel with 10% methanol in dichloromethane. The indoline obtained was dissolved in toluene and heated to reflux with 50 mg of 10% palladium/carbon for 4 hours. The catalyst was filtered off and washed with toluene. The combined filtrate and washings were evaporated to give 170 mg of 7-amino-6,7,8,9-tetrahydropyrido[1,2-a]indole.

b) 225 mg of di-t-butyl dicarbonate were added to a stirred solution of 175 mg of the product of a) and 112 mg of triethylamine in 20 ml of dichloromethane at 0° C. under a nitrogen atmosphere. After 18 hours, the solution was washed with saturated sodium bicarbonate solution, dried and evaporated to give an oil. Crystallization from diethyl ether gave 240 mg of 7-t-butoxyformamido-6,7,8,9-tetrahydropyrido[1,2-a]indole of melting point 137°–139° C.

c) 127 mg of oxalyl chloride were added to a solution of 240 mg of the product of b) in 30 ml of diethyl ether under a nitrogen atmosphere. After 10 minutes, the solvent was removed under reduced pressure and the residue was dissolved in 30 ml of dichloromethane. 170 mg of 1-methyl-3-indolylacetic acid and 200 mg of triethylamine were added to the resulting solution and the mixture was stirred for 72 hours. The solvent was removed under reduced pressure and the residue was purified by chromatography on silica gel with ethyl acetate/n-hexane (1:2). Crystallization from ethyl acetate/n-hexane gave 100 mg of 3-[7-t-butoxyformamido-6,7,8,9-tetrahydropyrido[1,2-a]indol-10-yl]-4-(1-methyl-3-indolyl)furan-2,5-dione of melting point 141°–145° C.

EXAMPLE 37

A saturated solution of hydrogen chloride in 30 ml of ethyl acetate was added to a stirred suspension of 60 mg of the pyrroledione product of Example 36 in 50 ml of ethyl acetate and the mixture was stirred for 18 hours. The solvent was removed under reduced pressure and the residue was triturated with ethyl acetate to give 35 mg of 3-[7-amino-6,7,8,9-tetrahydropyrido[1,2-a]indol-10-yl]-4-(1-methyl-3-indolyl)-1H-pyrrole-2,5-dione hydrochloride of melting point 260°–265° C.

EXAMPLE 38

A solution of 80 mg of 3-[8-t-butoxyformamido-6,7,8,9-tetrahydropyrido[1,2-a]indol-10-yl]-4-(1-methyl-3-indolyl)

furan-2,5-dione in 2 ml of dimethylformamide and 2 ml of 33% aqueous ammonia was heated to 100° C. for 1 hour. The solution was cooled and gave 60 mg of 3-[8-t-butoxyformamido-6,7,8,9-tetrahydropyrido[1,2-a]indol-10-yl]-4-(1-methyl-3-indolyl)-1H-pyrrole-2,5-dione of melting point 153°–155° C.

The furandione starting material was prepared as follows:

a) A solution of 300 mg of sodium hydroxide in 5 ml of water was added to a stirred solution of 1.35 g of the carboxylate product of Example 1b) in 25 ml of ethanol and the mixture was heated to reflux for 15 minutes. 2 ml of 2M hydrochloric acid and 10 ml of water were added and the precipitate obtained was filtered off and dried to give 1.14 g of 6,7,8,9-tetrahydropyrido[1,2-a]indole-8-carboxylic acid of melting point 244°–246° C.

b) A suspension of 900 mg of the product of a) in 1 ml of water and 20 ml of acetone was cooled to 0° C. and treated with 490 mg of triethylamine followed by 576 mg of ethyl chloroformate. After 0.5 hour, 345 mg of sodium azide in 1 ml of water were added and the mixture was stirred at 0° C. for 1 hour. The solvent was removed under reduced pressure and the residue was extracted with dichloromethane. The extracts were evaporated and the residue was purified by chromatography on silica gel with dichloromethane. The obtained solid was dissolved in 10 ml of toluene and heated to 100° C. for 4 hours under a nitrogen atmosphere. The solvent was evaporated to give 700 mg of 6,7,8,9-tetrahydropyrido[1,2-a]indole-8-isocyanate of melting point 87°–89° C.

c) 4 ml of a 2M sodium hydroxide solution were added to a solution of 700 mg of the product of b) in 50 ml of tetrahydrofuran and the solution obtained was stirred overnight. The solvent was removed under reduced pressure and the residue was extracted with dichloromethane. The dichloromethane extract was evaporated to give an amine which was redissolved in dichloromethane. 645 mg of di-t-butyl dicarbonate and 300 mg of triethylamine were added at 0° C. and the mixture was allowed to warm to room temperature while stirring for 72 hours. The mixture was washed with sodium bicarbonate solution and the organic phase was dried. The solvent was removed under reduced pressure and the residue was extracted with diethyl ether. The ethereal extracts were evaporated and the solid obtained was triturated with petroleum ether to give 550 mg of 8-t-butoxyformamido-6,7,8,9-tetrahydropyrido[1,2-a]indole of smelting point 155°–157° C.

d) 256 mg of oxalyl chloride were added to a solution of 550 mg of the product of c) in 10 ml of diethyl ether at 0° C. under a nitrogen atmosphere. After 1 hour, the solvent was removed under reduced pressure and the residue was dissolved in dichloromethane. Then, 363 mg of 1-methyl-3-indolylacetic acid and 390 mg of triethylamine were added and the mixture was stirred for 40 hours. The solvent was removed under reduced pressure and the residue was purified by chromatography on silica gel with ethyl acetate/ petroleum ether (1:2). Crystallization from diethyl ether/ petroleum ether gave 200 mg of 3-[8-t-butoxyformamido-6,7,8,9-tetrahydropyrido[1,2-a]indol-10-yl]-4-(1-methyl-3-indolyl)furan-2,5-dione of melting point 155°–160° C.

EXAMPLE 39

In a manner analogous to that described in Example 37, from the pyrroledione product of Example 38, there was prepared 3-[8-amino-6,7,8,9-tetrahydropyrido[1,2-a]indol-10-yl]-4-(1-methyl-3-indolyl)-1H-pyrrole-2,5-dione hydrochloride of melting point 310°–315° C.

EXAMPLE 40

A solution of 320 mg of 3-[4-(2-acetoxyethyl)-5,6-dihydro-4H-pyrrolo[3,2,1-ij]quinolin-1-yl]-4-(1-methyl-3-indolyl)furan-2,5-dione in 2 ml of dimethylformamide and 2 ml of 33% aqueous ammonia was heated to 140° C. for 12 hours. Water was added to the cooled mixture which was filtered to give 210 mg of a solid. A sample was crystallized from ethyl acetate to give 3-[4-(2-hydroxyethyl)-5,6-dihydro-4H-pyrrolo[3,2,1-ij]quinolin-1-yl]-4-(1-methyl-3-indolyl)-1H-pyrrole-2,5-dione of melting point 214°–215° C.

The furandione starting material was prepared as follows:

a) 25 ml of a 1.6M solution of n-butyllithium in n-hexane were added to a solution of 4.04 g of diisopropylamine in 20 ml of tetrahydrofuran at 0° C. under nitrogen. After 10 minutes, the stirred solution was cooled to −78° C. and a solution of 9.28 g of t-butyl acetate in 20 ml of tetrahydrofuran was added. After 10 minutes, 3.46 g of 1,2,5,6-tetrahydro-4H-pyrrolo[3,2,1-ij]quinolin-4-one in 20 ml of tetrahydrofuran was added followed by 8 ml of boron trifluoride diethyl etherate. The mixture was stirred at −78° C. and then 20 ml of pyrrolidine were added. The mixture was partitioned between ethyl acetate and water and the organic extracts were washed with water and sodium chloride solution, dried and evaporated. The residue was purified by chromatography on silica gel with ethyl acetate/ petroleum ether (1:3). There were obtained 4.1 g of t-butyl (E)-(1,2,5,6-tetrahydro-4H-pyrrolo[3,2,1-ij]quinolin-4-ylidene)acetate of melting point 105°–107° C.

b) A solution of 4 g of the product of a) in 400 ml of methanol was shaken with 280 mg of 10% palladium/carbon under a hydrogen atmosphere for 18 hours. The catalyst was filtered off and the filtrate was evaporated to an oil. 1.99 g of this oil in 100 ml of diethyl ether were treated with 5 ml of a 1M solution of lithium aluminum hydride in diethyl ether and the mixture was stirred for 2 hours. Water was added and the product was extracted with ethyl acetate. The ethyl acetate extracts were dried and concentrated under reduced pressure to give 1.44 g of 1,2,5,6-tetrahydro-4H-pyrrolo[3,2,1-ij]quinoline-4-ethanol.

c) 1.44 g of the product of b) in 40 ml of dichloromethane were treated with 10 ml of acetic anhydride and 5 ml of pyridine. The solution obtained was stirred and then evaporated. The residue was dissolved in dichloromethane. The solution was washed with water. The organic phase was separated, dried and concentrated to give 1.65 g of 4-(2-acetoxyethyl)-1,2,5,6-tetrahydro-4H-pyrrolo[3,2,1-ij] quinoline.

d) A solution of 1.6 g of the product of c) in 50 ml of xylene and 100 mg of 10% palladium/carbon was heated to reflux for 12 hours. The catalyst was filtered off and the filtrate was evaporated to give 1.7 g of 4-(2-acetoxyethyl)-5,6-dihydro-4H-pyrrolo[3,2,1-ij]quinoline.

e) 935 mg of oxalyl chloride were added to a stirred solution of 1.7 g of the product of c) in 45 ml of dichloromethane under a nitrogen atmosphere. After 1 hour, the solvent was removed under reduced pressure and the residue was dissolved in 90 ml of dichloromethane. Then, 1.38 g of 1-methyl-3-indolylacetic acid and 1.48 g of triethylamine were added to this solution and the mixture obtained was stirred for 18 hours. The solvent was removed under reduced pressure and the residue was purified by chromatography on silica gel with ethyl acetate/petroleum ether (1:2). Crystallization from methanol/water gave 280 mg of 3-[4-(2-acetoxyethyl)-5,6-dihydro-4H-pyrrolo[3,2,1-ij]-quinolin-1-yl]-4-(1-methyl-3-indolyl)furan-2,5-dione of melting point 143°–146° C.

EXAMPLE 41

A solution of 400 mg of 3-[8-[(t-butoxyformamido)methyl]-6,7,8,9-tetrahydropyrido[1,2-a]indol-10-yl]-4-(1-methyl-3-indolyl)furan-2,5-dione in 50 ml of dimethylformamide and 50 ml of water was treated with 2.5 g of hydroxylamine hydrochloride and 2.5 g of potassium carbonate and the solution obtained was heated to 100° C. The solvents were evaporated and the residue was dissolved in dichloromethane, washed with water and dried. The solvent was removed under reduced pressure and the residue was crystallized from ethyl acetate/petroleum ether to give 190 mg of 3-[8-[(t-butoxyformamido)methyl]-6,7,8,9-tetrahydropyrido[1,2-a]indol-10-yl]-1-hydroxy-4-(1-methyl-3-indolyl)pyrrole-2,5-dione of melting point 238°–240° C.

The furandione starting material was prepared as follows:

a) 2.4 g of methanesulfonic anhydride and 2 ml of triethylamine were added to a stirred solution of 2.01 g of 6,7,8,9-tetrahydropyrido[1,2-a]indole-8-methanol in 40 ml of dichloromethane under a nitrogen atmosphere. After 18 hours, the mixture was washed with saturated sodium bicarbonate solution, dried and evaporated to an oil. Then, 1.8 g of this oil were dissolved in 10 ml of isopropanol and 5 ml of 33% aqueous ammonia and the mixture was heated to 80° C. for 10 hours. The solvent was removed under reduced pressure and the residue was partitioned between dichloromethane and saturated sodium bicarbonate solution. The organic phase was dried and evaporated to give 1.3 g of 8-aminomethyl-6,7,8,9-tetrahydropyrido[1,2-a]indole of melting point 85°–90° C.

b) 1.09 g of di-t-butyl dicarbonate were added to a stirred solution of 890 mg of 8-aminomethyl-6,7,8,9-tetrahydropyrido[1,2-a]indole and 920 mg of triethylamine in 60 ml of dichloromethane at 0° C. under a nitrogen atmosphere. After 72 hours, the organic phase was washed with saturated sodium bicarbonate solution, dried and evaporated. The residue was crystallized from petroleum ether to give 1.03 g of 8-[(t-butoxyformamido)methyl]-6,7,8,9-tetrahydropyrido[1,2-a]indole of melting point 80°–85° C.

c) 445 mg of oxalyl chloride were added dropwise to a solution of 1 g of the product of b) in 20 ml of diethyl ether under a nitrogen atmosphere at 0° C. After 1 hour, the solvent was removed under reduced pressure and the residue was dissolved in dichloromethane. Then, 630 mg of 1-methyl-3-indolylacetic acid and 920 µl of triethylamine were added to this solution and the mixture was stirred for 72 hours. The solvent was removed under reduced pressure and the residue was purified by chromatography on silica gel with ethyl acetate/petroleum ether (1:2). The resulting solid was crystallized from diethyl ether and there were obtained 315 mg of 3-[8-[(t-butoxyformamido)methyl]-6,7,8,9-tetrahydropyrido[1,2-a]indol-10-yl]-4-(1-methyl-3-indolyl)furan-2,5-dione of melting point 124°–126° C.

EXAMPLE 42

In a manner analogous to that described in Example 37, from the product of Example 41, there was prepared 3-[8-(aminomethyl)-6,7,8,9-tetrahydropyrido[1,2-a]indol-10-yl]-1-hydroxy-4-(1-methyl-3-indolyl)pyrrole-2,5-dione hydrochloride of melting point 280°–282° C.

EXAMPLE 43

In a manner analogous to that described in Example 11, from the product of Example 40, there was prepared 3-[4-[2-(amidinothio)ethyl]-5,6-dihydro-4H-pyrrolo[3,2,1-ij]quinolin-1-yl]-4-(1-methyl-3-indolyl)-1H-pyrrole-2,5-dione methanesulfonate of melting point 185°–190° C.

EXAMPLE 44

In a manner analogous to that described in Example 2, from the product of Example 40, there was prepared 3-[4-(2-aminoethyl)-5,6-dihydro-4H-pyrrolo[3,2,1-ij]quinolin-1-yl]-4-(1-methyl-3-indolyl)-1H-pyrrole-2,5-dione hydrochloride of melting point 193°–195° C.

EXAMPLE 45

In a manner analogous to that described in Example 2, from the product of Example 26, there was obtained 3-[8-(aminomethyl)-6,7,8,9-tetrahydropyrido[1,2-a]indol-10-yl]-4-(3-benzo[b]thienyl)-1H-pyrrole-2,5-dione hydrochloride of melting point 285°–287° C.

EXAMPLE 46

In a manner analogous to that described in the first paragraph of Example 1, from 3-[8-(acetoxymethyl)-6,7,8,9-tetrahydropyrido[1,2-a]indol-10-yl]-4-(2-naphthyl)furan-2,5-dione (obtained as described in the last paragraph of Example 1 by using 2-naphthylacetic acid in place of 1-methyl-3-indolylacetic acid), there was prepared 3-[6,7,8,9-tetrahydro-8-(hydroxymethyl)pyrido[1,2-a]indol-10-yl]-4-(2-naphthyl)-1H-pyrrole-2,5-dione of melting point 260°–263° C.

EXAMPLE 47

In a manner analogous to that described in Example 2, from the product of Example 46, there was obtained 3-[8-(aminomethyl)-6,7,8,9-tetrahydropyrido[1,2-a]indol-10-yl]-4-(2-naphthyl)-1H-pyrrole-2,5-dione hydrochloride of melting point >300° C.

EXAMPLE 48

In an analogous manner to that described in Example 10, from the product of Example 27, there was prepared 3-[8-(aminomethyl)-6,7,8,9-tetrahydropyrido[1,2-a]indol-1-yl]-4-(1-naphthyl)-1H-pyrrole-2,5-dione of melting point 167°–169° C.

EXAMPLE 49

In a manner analogous to that described in the first paragraph of Example 1, from 1.3 g of 3-[9-(acetoxymethyl)-7,8,9,10-tetrahydro-6H-azepino[1,2-a]indol-11-yl]-4-(1-methyl-3-indolyl)furan-2,5-dione, there were obtained 520 mg of 3-[7,8,9,10-tetrahydro-9-(hydroxymethyl)-6H-azepino[1,2-a]indol-11-yl]-4-(1-methyl-3-indolyl)-1H-pyrrole-2,5-dione of melting point 268°–270° C.

The furandione starting material was prepared as follows:

a) A solution of 18.9 g of ethyl indole-2-carboxylate in 100 ml of dimethylformamide was added to a suspension of 2.64 g of sodium hydride in 50 ml of dimethylformamide. After 1 hour, a solution of 20.9 g of ethyl 5-bromovalerate in 100 ml of dimethylformamide was added dropwise. After 48 hours, the mixture was poured into water, extracted with dichloromethane and the combined dichloromethane extracts were washed with water, dried and concentrated to give 26.2 g of ethyl 1-(4-ethoxycarbonylbutyl)indole-2-carboxylate.

b) This oil was dissolved in 50 ml of tetrahydrofuran and the solution was added to a stirred suspension of 11.2 g of potassium t-butoxide in 150 ml of tetrahydrofuran. After 36 hours, the mixture was concentrated and the residue was poured into a mixture of water and diethyl ether. The organic phase was dried and concentrated. Chromatography of the residue on silica gel with dichloromethane/methanol (9:1) gave a solid which was recrystallized from ethyl acetate/n-hexane, and there were obtained 6.1 g of ethyl 7,8-dihydro-10-hydroxy-6H-azepino[1,2-a]indole-9-carboxylate of melting point 74°–81° C.

c) 5.5 g of this solid were dissolved in 200 ml of ethanol and treated with 11 spoon spatula measures of Raney nickel and 400 ml of water. The mixture was heated at reflux for 4 hours. The cooled mixture was filtered and the residue was washed with ethyl acetate. The filtrate was extracted with ethyl acetate. The combined extracts and washings were dried and concentrated to give an oil which was purified by chromatography on silica gel with dichloromethane, and there were obtained 2.5 g of ethyl 7,8,9,10-tetrahydro-6H-azepino[1,2-a]indole-9-carboxylate of melting point 69°–70° C.

d) This solid was dissolved in 50 ml of tetrahydrofuran and added dropwise to a mixture of 0.45 g of lithium aluminum hydride in 20 ml of tetrahydrofuran. The mixture was stirred for 2 hours and then water was added. The resulting mixture was extracted with diethyl ether and the combined extracts were dried and concentrated. Chromatography of the residue on silica gel with dichloromethane gave 1.90 g of 7,8,9,10-tetrahydro-9-(hydroxymethyl)-6H-azepino[1,2-a]indole of melting point 109°–111° C.

e) 1.8 g of this solid were dissolved in 100 ml of diethyl ether at 0° C. and treated with 1.70 g of acetic anhydride and 0.66 g of pyridine. After 8 hours, an additional 5 g of pyridine were added and the mixture was stirred for 76 hours. The solvents were removed under reduced pressure and the residue was chromatographed on silica gel with dichloromethane, and there were obtained 1.98 g of 9-(acetoxymethyl)-7,8,9,10-tetrahydro-6H-azepino[1,2-a]indole of melting point 65° C.

f) 1.90 g of this solid were dissolved in 50 ml of dichloromethane. The solution was cooled to 0° C. and treated with 1.03 g of oxalyl chloride. After 2 hours, the solvent was removed by evaporation and the residue was dissolved in dichloromethane and added dropwise to a solution of 1.5 g of 1-methylindole-3-acetic acid and 1.86 g of triethylamine in dichloromethane. The mixture was concentrated and the residue was chromatographed on silica gel with dichloromethane containing 5% methanol by volume. The solid obtained was recrystallized from ethyl acetate/n-hexane to give 1.55 g of 3-[9-(acetoxymethyl)-7,8,9,10-tetrahydro-6H-azepino[1,2-a]indol-11-yl]-4-(1-methyl-3-indolyl)furan-2,5-dione of melting point 164°–166° C.

EXAMPLE 50

In a manner analogous to that described in Example 12, from 0.50 g of 3-[7,8,9,10-tetrahydro-6H-azepino[1,2-a]indol-11-yl]-3-(1-methyl-3-indolyl)furan-2,5-dione, there was obtained 0.43 g of 3-[7,8,9,10-tetrahydro-6H-azepino[1,2-a]indol-11-yl]-3-(1-methyl-3-indolyl)-1H-pyrrole-2,5-dione of melting point >300° C.

The furandione starting material was prepared as follows:

1.5 g of oxalyl chloride were added dropwise to an ice-cold solution of 2.0 g of 7,8,9,10-tetrahydro-6H-azepino[1,2-a]indole (J. Org. Chem. 33, 1968, 4286) in 50 ml of dichloromethane. The mixture was stirred for 2 hours. The solvent was removed in a vacuum and the residue was dissolved in dichloromethane. The solution obtained was added to a solution of 2.2 g of 1-methyl-3-indolylacetic acid and 2.73 g of triethylamine in 50 ml of dichloromethane. The mixture was stirred and then concentrated. The residue was chromatographed on silica gel with dichloromethane and there was obtained 1.0 g of 3-[7,8,9,10-tetrahydro-6H-azepino[1,2-a]indol-11-yl]-3-(1-methyl-3-indolyl)furan-2,5-dione of melting point 257°–259° C.

EXAMPLE 51

A solution of 150 mg of the product of Example 49 and 146 mg of 2,6-lutidine in 15 ml of dichloromethane was added to a solution of 290 mg of trifluoromethanesulfonic anhydride at 0° C. After 3 hours, 25 ml of 33% aqueous ammonia were added and the mixture was stirred for 16 hours. The mixture was extracted with dichloromethane and the combined extracts were dried and concentrated. Chromatography of the residue on silica gel with dichloromethane/methanol/acetic acid/water (90:18:3:2) gave 50 mg of 3-[9-(aminomethyl)-7,8,9,10-tetrahydro-6H-azepino[1,2-a]indol-11-yl]-4-(1-methyl-3-indolyl)-1H-pyrrole-2,5-dione acetate of melting point 215° C. (decomposition).

EXAMPLE 52

A mixture of 40 mg of the product of Example 51, 20 mg of sodium bicarbonate and 25 mg of 3,5-dimethyl-$N^2$-nitro-1-pyrazole-1-carboxamide in 10 ml of ethanol was heated at reflux for 16 hours. The mixture was concentrated and the residue was chromatographed on silica gel with dichloromethane/methanol (9:1). There were obtained 15 mg of 3-(1-methyl-3-indolyl)-4-[7,8,9,10-tetrahydro-9-[(2-nitroguanidino)methyl]-6H-azepino[1,2-a]indol-11-yl]-1H-pyrrole-2,5-dione of melting point 177°–178° C.

EXAMPLE 53

In a manner analogous to that described in the first paragraph of Example 1, from 0.20 g of 3-[8-(acetoxymethyl)-7,8,9,10-tetrahydro-6H-azepino[1,2-a]indol-11-yl]-4-(1-methyl-3-indolyl)furan-2,5-dione, there were obtained 60 mg of 3-[7,8,9,10-tetrahydro-8-(hydroxymethyl)-6H-azepino[1,2-a]indol-11-yl]-4-(1-methyl-3-indolyl)-1H-pyrrole-2,5-dione of melting point 109°–111° C.

The furandione starting material was prepared as follows:

a) A solution of 5 g of ethyl 6,7-dihydro-9-hydroxypyrido[1,2-a]indole-8-carboxylate (prepared as described in Example 1) in 200 ml of dimethylformamide was treated with 550 mg of sodium hydride. The mixture was stirred under a nitrogen atmosphere and then a solution of 3.6 g of ethyl bromoacetate in 50 ml of dimethylformamide was added. After 16 hours, the mixture was poured into water and extracted with diethyl ether. The combined extracts were washed with water, dried and concentrated to give 4.4 g of ethyl 8-(ethoxycarbonyl)-6,7,8,9-tetrahydro-9-oxopyrido[1,2-a]indole-8-acetate.

b) A solution of 5.0 g of the product of a) in 200 ml of tetrahydrofuran was added dropwise to a stirred solution of 2.0 g of potassium t-butoxide in 50 ml of tetrahydrofuran. The mixture was stirred and then 1 ml of glacial acetic acid was added. The mixture was poured into water and extracted with dichloromethane. The combined extracts were dried and concentrated. The residue was chromatographed on silica gel with dichloromethane/methanol (95:5) to give 3.0 g of diethyl 7,8-dihydro-10-hydroxy-6H-azepino[1,2-a]indole-8,9-dicarboxylate.

c) A mixture of 2.8 g of the product of b) and 0.5 g of boric acid was heated at 150° C. for 1 hour and at 170° C. for 3 hours. Ice-water was added to the cooled mixture and the whole was extracted with dichloromethane. The combined dichloromethane extracts were dried and concentrated. The residue was chromatographed on silica gel with dichloromethane/methanol (95:5). There were obtained 2.1 g of ethyl 7,8,9,10-tetrahydro-10-oxo-6H-azepino[1,2-a]indole-8-carboxylate.

d) 2.1 g of the product of c) were dissolved in 80 ml of ethanol and treated with 4 spoon spatula measures of Raney nickel and 50 ml of water. The mixture was heated at reflux for 4 hours, cooled and filtered, and the residue was washed with ethyl acetate. The filtrate was extracted with ethyl acetate. The combined extracts and washings were dried and concentrated. Chromatography of the residue on silica gel with dichloromethane gave 0.89 g of ethyl 7,8,9,10-tetrahydro-6H-azepino[1,2-a]indole-8-carboxylate.

e) 0.85 g of the product of d) was dissolved in 50 ml of tetrahydrofuran and added dropwise to a stirred suspension of 140 mg of lithium aluminum hydride in 50 ml of tetrahydrofuran. After the addition of water, the mixture was extracted with diethyl ether. The combined extracts were dried and concentrated. Chromatography of the residue on silica gel with dichloromethane/methanol (95:5) gave 0.70 g of 7,8,9,10-tetrahydro-8-(hydroxymethyl)-6H-azepino[1,2-a]indole of melting point 90°–91° C.

f) 0.70 g of the product of e) was treated with 0.66 g of acetic anhydride and 0.39 g of pyridine in 50 ml of diethyl ether. An additional 1 g of pyridine and an additional 1 g of acetic acid were added and the mixture was stirred for 16 hours. Then, the mixture was concentrated and the residue was chromatographed on silica gel with dichloromethane, and there were obtained 0.60 g of 8-(acetoxymethyl)-7,8,9,10-tetrahydro-6H-azepino[1,2-a]indole of melting point 77°–79° C.

9) A solution of 0.60 g of the product of f) in 50 ml of dichloromethane was treated dropwise with 0.33 g of oxalyl chloride. After allowing the solution to stand at 10° C. for 2 hours, the solution was concentrated and the residue was dissolved in dichloromethane. The solution was added to a solution of 0.49 g of 1-methylindole-3-acetic acid and 0.59 g of triethylamine in dichloromethane. After 16 hours, the mixture was concentrated and the residue was chromatographed on silica gel with dichloromethane/methanol (95:5). There was obtained 0.51 g of 3-[8-(acetoxymethyl)-7,8,9,10-tetrahydro-6H-azepino[1,2-a]indol-11-yl]-4-(1-methyl-3-indolyl)furan-2,5-dione of melting point 70° C.

EXAMPLE 54

A solution of 60 mg of the product of Example 53 and 60 mg of 2,6-lutidine in 25 ml of dichloromethane was added dropwise to a solution of 116 mg of trifluoromethanesulfonic anhydride in 25 ml of dichloromethane at 0° C. After 3 hours, 25 ml of aqueous ammonia were added to the solution. The organic phase was dried and concentrated. Chromatography of the residue on silica gel gave 30 mg of 3-[8-(aminomethyl)-7,8,9,10-tetrahydro-6H-azepino[1,2-a]indol-11-yl]-4-(1-methyl-3-indolyl)-1H-pyrrole-2,5-dione acetate of melting point 162°–163° C.

EXAMPLE 55

A solution of 0.64 g of the product of Example 1 and 0.4 ml of 2,4,6-collidine in 20 ml of dichloromethane was added dropwise to a solution of 0.75 g of trifluoromethanesulfonic anhydride in 10 ml of dichloromethane at 0° C. After 2.5 hours, the mixture was treated with 3 ml of piperidine and stirred for 16 hours. Concentration and chromatography of the residue on silica gel with dichloromethane/methanol (gradient from 98:2 to 50:50) gave 340 mg of 3-[6,7,8,9-tetrahydro-8-[(1-piperidino)methyl]pyrido[1,2-a]indol-10-yl]-4-(1-methyl-3-indolyl)-1H-pyrrole-2,5-dione. This was converted into the hydrochloride of melting point 294° C. (decomposition), by treatment with a saturated solution of hydrogen chloride in ethyl acetate.

EXAMPLE 56

A solution of 0.8 g of the product of Example 1 and 0.44 g of 2,4,6-collidine in 30 ml of dichloromethane was added to a solution of 0.9 g of trifluoromethanesulfonic anhydride in 10 ml of dichloromethane at 0° C. After 1.5 hour, the mixture was treated with 3.64 g of diisopropylamine and stirred for 16 hours. The mixture was washed with water and then with saturated aqueous sodium bicarbonate solution, dried and concentrated. The solid obtained was dissolved in ethyl acetate and treated wish a saturated solution of hydrogen chloride in ethyl acetate. Removal of the solvent in vacuo gave 260 mg of 3-[6,7,8,9-tetrahydro-8-[(diisopropylamino)methyl]pyrido[1,2-a]indol-10-yl]-4-(1-methyl-3-indolyl)-1H-pyrrole-2,5-dione hydrochloride of melting point 187° C. (decomposition).

EXAMPLE 57

A solution of 1.0 g of 3-[8-(acetoxymethyl)-6,7,8,9-tetrahydropyrido[1,2-a]indol-10-yl]-4-(3-benzofuranyl)furan-2,5-dione in 100 ml of chloroform was treated with 13.8 ml of hexamethyldisilazane and 2.73 ml of methanol and the solution obtained was heated to 50° C. while stirring under a nitrogen atmosphere for 6 hours. An additional 13.8 ml of hexamethyldisilazane and 2.73 ml of methanol were added and the heating was continued for 16 hours. Two more additions of the same quantities of hexamethyldisilazane and methanol were effected and the temperature of the mixture was held at 50° C. for an additional 24 hours. Then, 20 ml of methanol were added and the mixture was heated to reflux for 15 minutes, cooled and concentrated. The precipitate was filtered off and triturated in succession with ethyl acetate and methanol. There were obtained 630 mg of 3-[8-(acetoxymethyl)-6,7,8,9-tetrahydropyrido[1,2-a]indol-10-yl]-4-(3-benzofuranyl)-1H-pyrrole-2,5-dione of melting point 234°–237° C.

The furandione starting material was prepared as follows:

1.7 g of oxalyl chloride were added dropwise to a solution of 3.3 g of 8-(acetoxymethyl)-6,7,8,9-tetrahydropyrido[1,2-a]indole in 200 ml of diethyl ether under a nitrogen atmosphere. After 15 minutes the solvent was removed under reduced pressure and the residue was dissolved in dichloromethane. Then, 2.4 g of 3-benzofuranylacetic acid and 5.6 ml of triethylamine were added to this solution and the mixture was stirred overnight. The solvent was removed under reduced pressure and the residue was purified by chromatography on silica gel with ethyl acetate/petroleum ether (1:2). Crystallization of the residue from ethyl acetate/petroleum ether gave 1.62 g of 3-[8-(acetoxymethyl)-6,7,8,9-tetrahydropyrido[1,2-a]indol-10-yl]-4-(3-benzofuranyl)furan-2,5-dione of melting point 214°–215° C.

EXAMPLE 58

A solution of 300 mg of the product of Example 57 in 40 ml of methanol was treated with 5 ml of 2M sodium hydroxide. After 10 minutes, the mixture was acidified with 5 ml of 2M hydrochloric acid and the methanol was removed under reduced pressure. The residue was partitioned between ethyl acetate and water. The phases were separated and the organic phase was washed with sodium bicarbonate solution and dried. The solution was concentrated and the precipitate was filtered off to give 190 mg of 3-(3-benzofuranyl)-4-[6,7,8,9-tetrahydro-8-(hydroxymethyl)pyrido-[1,2-a]indol-10-yl]-1H-pyrrole-2,5-dione of melting point 246°–248° C.

EXAMPLE 59

In a manner analogous to that described in Example 2, from the product of Example 58, there was prepared 3-[8-(aminomethyl)-6,7,8,9-tetrahydropyrido[1,2-a]indol-10-yl]-4-(3-benzofuranyl)-1H-pyrrole-2,5-dione hydrochloride of melting point 210°–212° C.

EXAMPLE 60

118 mg of trifluoromethanesulfonic anhydride in 20 ml of dichloromethane were treated at 0° C. under a nitrogen atmosphere with a suspension of 90 mg of the product of Example 26 and 45 mg of collidine in 20 ml of dichloromethane. After 45 minutes, 0.41 ml of a 40% solution of dimethylamine in water was added and the mixture was stirred for 1.5 hours. The solution obtained was washed with water and sodium bicarbonate solution, and dried. The solution was concentrated and the resulting crystals were filtered off and dried to give 60 mg of 3-(3-benzo[b]thienyl)-4-[6,7,8,9-tetrahydro-8-(dimethylaminomethyl)pyrido[1,2-a]indol-10-yl]-1H-pyrrole-2,5-dione of melting point 285°–286° C.

EXAMPLE 61

546 mg of trifluoromethanesulphonic anhydride in 80 ml of dichloromethane were treated at 0° C. under a nitrogen atmosphere with a suspension of 400 mg of the product of Example 19 and 208 mg of collidine in 120 ml of dichloromethane. After 1 hour, 1.9 ml of 40% aqueous dimethylamine were added and the mixture was stirred for 3 hours. The solvent was removed and the residue was subjected to chromatography on silica gel with dichloromethane/methanol/acetone (88:10:2). Trituration with ethyl acetate followed by recrystallization from methanol gave 295 mg of 3-[2,3-dihydro-2-(dimethylaminomethyl)-1H-pyrrolo[1,2-a]indol-9-yl]-4-(1-methyl-3-indolyl)-1H-pyrrole-2,5-dione trifluoromethanesulphonate of melting point 323°–325° C.

EXAMPLE 62

A solution of 400 mg of 3-[8-cyano-6,7,8,9-tetrahydropyrido[1,2-a]indol-10-yl]-4-(1-methyl-3-indolyl)furan-2,5-dione in 12 ml of dimethylformamide and 12 ml of 33% aqueous ammonia was heated to 140° C. for 3 hours. The mixture was cooled and the resulting solid was filtered off and dried to give 275 mg of 3-[8-cyano-6,7,8,9-tetrahydropyrido-[1,2-a]indol-10-yl]-4-(1-methyl-3-indolyl)-1H-pyrrole-2,5-dione of melting point 312°–313° C.

The furandione starting material was prepared as follows:

a) A suspension of 4.0 g of the product of Example 38a) in 4.4 ml of water and 84 ml of acetone was cooled to 0° C. and 2.18 g of triethylamine were added. Thereafter, 2.56 g of ethyl chloroformate were added and the resulting solution was stirred under a nitrogen atmosphere. Then, 0.9 ml of 33% aqueous ammonia were added and the mixture was allowed to warm to room temperature. An additional 0.5 ml of 33% aqueous ammonia was added and stirring was continued. The solvent was evaporated and the residue was extracted with of dichloromethane. The organic phase was washed with of water, dried and concentrated to give 2.8 g of 6,7,8,9-tetrahydropyrido[1,2-a]indole-8-carboxamide of melting point 179°–181° C.

b) 991 mg of trifluoroacetic anhydride were added dropwise to a suspension of 1.0 g of 6,7,8,9-tetrahydropyrido[1,2-a]indole-8-carboxamide in 15 ml of dioxane at 10° C. The mixture was partitioned between dichloromethane and water and the organic phase was dried. The solvent was removed under reduced pressure to give an oil which was subjected to chromatography on silica gel with ethyl acetate/petroleum ether (1:1). There were obtained 740 mg of 6,7,8,9-tetrahydropyrido[1,2-a]indole-8-carbonitrile of melting point 116°–118° C.

c) 518 mg of oxalyl chloride were added to a solution of 800 mg of 6,7,8,9-tetrahydropyrido[1,2-a]indole-8-carbonitrile in 100 ml of diethyl ether under a nitrogen atmosphere. The solvent was evaporation and the residue was dissolved in dichloromethane. Then, 771 mg of 1-methyl-3-indolylacetic acid and 1.24 g of triethylamine were added to this solution and the mixture was stirred overnight. The solvent was removed under reduced pressure and the residue was purified by chromatography on silica gel with 10% methanol in dichloromethane. The fractions containing the desired product were concentrated and the crystals obtained were filtered off and dried to give 560 mg of 3-[8-cyano-6,7,8,9-tetrahydropyrido[1,2-a]indol-10-yl]-4-(1-methyl-3-indolyl)furan-2,5-dione of melting point 309°–311° C.

EXAMPLE 63

Hydrogen chloride gas was bubbled through a solution of 200 mg of the product of Example 62 in 250 ml of methanol at 0° C. The solvent was then removed under reduced pressure and the residue was dissolved in 50 ml of dichloromethane and 250 ml of ethanol. Ammonia was bubbled through the solution and the solvent was then evaporated. The residue was purified by chromatography on silica gel with dichloromethane/methanol/acetic acid/water (90:18:3:2). Trituration with ethyl acetate gave 75 mg of 3-[8-amidino-6,7,8,9-tetrahydropyrido[1,2-a]indol-10-yl]-4-(1-methyl-3-indolyl)-1H-pyrrole-2,5-dione hydrochloride of melting point 237°–239° C.

EXAMPLE 64

A Solution of 50 mg of 3-[8-carbamoyl-6,7,8,9-tetrahydropyrido[1,2-a]indol-10-yl]-4-(1-methyl-3-indolyl)furan- 2,5-dione in 4 ml of dimethylformamide and 4 ml of 33% aqueous ammonia was heated to 140° C. The mixture was extracted with ethyl acetate and the organic phase was washed with water and then dried. The majority of the solvent was evaporated and the precipitate obtained was filtered off and dried. There were obtained 20 mg of 3-[8-carbamoyl-6,7,8,9-tetrahydropyrido[1,2-a]indol-10-yl]-4-(1-methyl-3-indolyl)-1H-pyrrole-2,5-dione of melting point 315°–316° C.

The furandione starting material was prepared as follows:

178 mg of oxalyl chloride were added to a solution of 300 mg of the product of Example 62a) in 40 ml of dichloromethane under a nitrogen atmosphere. Thereafter, the solvent was removed under reduced pressure and the residue was dissolved in dichloromethane. Then, 265 mg of 1-methyl-3-indolylacetic acid and 424 mg of triethylamine were added and the mixture was stirred for about 60 hours. The solvent was removed under reduced pressure and the residue was purified by chromatography on silica gel with 10% methanol in dichloromethane. Crystallization from ethyl acetate gave 70 mg of 3-[8-carbamoyl-6,7,8,9-tetrahydropyrido[1,2-a]indol-10yl]-4-(1-methyl-3-indolyl)furan-2,5-dione of melting point 307°–309° C.

EXAMPLE 65

In a manner analogous to that described in the first paragraph of Example 1, from 3-[8-(acetoxymethyl)-6,7,8,9-tetrahydropyrido[1,2-a]indol-10-yl]-4-(5-methoxy-1-methyl-3-indolyl)furan-2,5-dione, there was prepared 3-[6,7,8,9-tetrahydro-8-(hydroxymethyl)pyrido[1,2-a]indol-10-yl]-4-(5-methoxy-1-methyl-3-indolyl)-1H-pyrrole-2,5-dione of melting point 300°–303° C.

The furandione starting material was prepared as follows:

0.4 ml of oxalyl chloride were added to a solution of 906 mg of 8-(acetoxymethyl)-6,7,8,9-tetrahydropyrido[1,2-a]indole in 35 ml of diethyl ether under a nitrogen atmosphere. Thereafter, the solvent was removed under reduced pressure and the residue was dissolved in 120 ml of dichloromethane. Then, 940 mg of 5-methoxy-1-methyl-3-indolylacetic acid and 1.16 ml of triethylamine were added and the mixture was stirred for 40 hours. The solvent was removed under reduced pressure and the residue was purified by chromatography on silica gel with ethyl acetate/n-hexane (1:2). Crystallization from ethyl acetate/petroleum ether gave 250 mg of 3-[8-(acetoxymethyl)-6,7,8,9-tetrahydropyrido[1,2-a]indol-10-yl]-4-(5-methoxy-1-methyl-3-indolyl)furan-2,5-dione of melting point 259°–261° C.

EXAMPLE 66

In a manner analogous to that described in Example 2, from the product of Example 65, there was prepared 3-[8-(aminomethyl)-6,7,8,9-tetrahydropyrido[1,2-a]indol-10-yl]-4-(5-methoxy-1-methyl-3-indolyl)-1H-pyrrole-2,5-dione hydrochloride of melting point 268°–270° C.

EXAMPLE 67

In a manner analogous to that described in the first paragraph of Example 1, from 3-[8-(acetoxymethyl)-6,7,8,9-tetrahydropyrido[1,2-a]indol-10-yl]-4-(5-bromo-1-methyl-3-indolyl)furan-2,5-dione, there was prepared 3-[6,7,8,9-tetrahydro-8-(hydroxymethyl)pyrido[1,2-a]indol-10-yl]-4-(5-bromo-1-methyl-3-indolyl)-1H-pyrrole-2,5-dione of melting point 316°–318° C.

The furandione starting material was prepared as follows:

a) 500 mg of a 60% dispersion of sodium hydride in mineral oil were added to solution of 1 g of 5-bromoindole-3-acetic acid in 50 ml of tetrahydrofuran and the mixture was stirred under a nitrogen atmosphere for 1 hour. Thereafter, 820 mg (5.8 mmol) of methyl iodide were added and the mixture was stirred under a nitrogen atmosphere for 24 hours. Then, 5 ml of water were added and the solvent was removed under reduced pressure. The residue was treated with 2M hydrochloric acid and the precipitate formed was filtered off, washed with n-hexane and dried. The obtained solid was recrystallized from diethyl ether to give 5-bromo-1-methyl-3-indolylacetic acid of melting point 192°–194° C.

b) 500 mg of oxalyl chloride were added to a solution of 900 mg of 8-(acetoxymethyl)-6,7,8,9-tetrahydropyrido[1,2-a]indole in 100 ml of diethyl ether under a nitrogen atmosphere. Thereafter, the solvent was evaporated and the residue was dissolved in dichloromethane. Then, 880 mg of 5-bromo-1-methyl-3-indolylacetic acid and 810 mg of triethylamine were added and the mixture was stirred for 48 hours. The solvent was removed under reduced pressure and the residue was purified by chromatography on silica gel with ethyl acetate/n-hexane (1:1) to give 400 mg of a solid. A sample was recrystallized from ethyl acetate to give 3-[8-(acetoxymethyl)-6,7,8,9-tetrahydropyrido[1,2-a]indol-10-yl]-4-(5-bromo-1-methyl-3-indolyl)furan-2,5-dione of melting point 215°–220° C.

EXAMPLE 68

In a manner analogous to that described in Example 2, from the product of Example 67, there was prepared 3-[8-(aminomethyl)-6,7,8,9-tetrahydropyrido[1,2-a]indol-10-yl]-4-(5-bromo-1-methyl-3-indolyl)-1H-pyrrole-2,5-dione hydrochloride of melting point >310° C.

EXAMPLE 69

A solution of 200 mg of 3-[7-(2-acetoxyethyl)-6,7,8,9-tetrahydropyrido[1,2-a]indol-10-yl]-4-(1-methyl-3-indolyl)-furan-2,5-dione in 2 ml of dimethylformamide and 1 ml of 33% aqueous ammonia was heated to 140° C. Then, 1 ml of a 2M solution of sodium hydroxide was added to the cooled solution and the mixture was stirred for 2 hours. The mixture was acidified with 2M hydrochloric acid and evaporated. The residue was partitioned between ethyl acetate and water and the organic phase was dried. The solvent was evaporated and the solid obtained was triturated with ethyl acetate to give 115 mg of 3-[6,7,8,9-tetrahydro-7-(2-hydroxyethyl)pyrido[1,2-a]indol-10-yl]-4-(1-methyl-3-indolyl)-1H-pyrrole-2,5-dione of melting point 236°–238° C.

The furandione starting material was prepared as follows:

a) 400 mg of a 60% dispersion of sodium hydride in mineral oil were added to a solution of 2.24 g of triethyl phosphonoacetate in 40 ml of dimethoxyethane under a nitrogen atmosphere. Then, the solution was cooled to 0° C. and 1.85 g of the product of Example 35d) in 10 ml of dimethoxyethane were added. The mixture was stirred overnight and then evaporated. The residue was dissolved in dichloromethane. The solution was washed with water, dried and concentrated. The residue was purified by chromatography on silica gel with diethyl ether/petroleum ether (1:3), and there were obtained 1.55 g of a mixture of ethyl (E) and (Z)-(6,7,8,9-tetrahydropyrido[1,2-a]indol-7-ylidene)acetate. Then, 1.4 g thereof were dissolved in ethanol and the solution was shaken with 280 mg of 10% palladium/carbon under a hydrogen atmosphere. The catalyst was then filtered off and the filtrate was evaporated to give 1.2 g of ethyl 6,7,8,9-tetrahydropyrido[1,2-a]indole-7-acetate of melting point 66°–68° C. after crystallization from diethyl ether/petroleum ether.

b) A solution of 1.2 g of the product of a) in 100 ml of diethyl ether was treated with 3.5 ml of a 1M solution of lithium aluminum hydride in diethyl ether. After stirring for 1 hour, the mixture was quenched with 50 ml of aqueous ammonium chloride. The mixture was extracted with 150 ml of diethyl ether and the organic phase was dried and evaporated to give 1.01 g of 6,7,8,9-tetrahydro-7-(2-hydroxyethyl)pyrido[1,2-a]indole of melting point 70°–72° C after crystallization from diethyl ether/petroleum ether.

c) A solution of 1.04 g of the product of b), in 30 ml of dichloromethane was treated with 6 ml of acetic anhydride and 3 ml of pyridine and the solution was stirred under a nitrogen atmosphere. The mixture was then evaporated to dryness and the residue was dissolved in dichloromethane. The organic phase was washed with 2M hydrochloric acid and with water, dried and evaporated. The residue was purified by chromatography on silica gel with diethyl ether/ petroleum ether (1:4) to give 670 mg of 7-(2-acetoxyethyl) -6,7,8,9-tetrahydropyrido[1,2-a]indole.

d) 250 μl of oxalyl chloride were added to a solution of 670 mg of the product of c) in 12 ml of dichloromethane under a nitrogen atmosphere. The solvent was removed under reduced pressure and the residue was dissolved in dichloromethane. Thereafter, 493 mg of 1-methyl-3-indolylacetic acid and 527 mg of triethylamine were added to this solution and the mixture was stirred. Then, the solvent was removed under reduced pressure and the residue was purified by chromatography on silica gel with ethyl acetate/ petroleum ether (1:2) to give 350 mg of 3-[7-(2-acetoxyethyl)-6,7,8,9-tetrahydropyrido[1,2-a]indole -10-yl]-4-(1-methyl-3-indolyl)furan-2,5-dione of melting point 182°–184° C. after crystallization from ethyl acetate.

EXAMPLE 70

In a manner analogous to that described in Example 2, from the product of Example 69, there was prepared 3-[7-(2-aminoethyl)-6,7,8,9-tetrahydropyrido[1,2-a]indol-10-yl]-4-(1-methyl-3-indolyl)-1H-pyrrole-2,5-dione hydrochloride of melting point 240°–242° C.

EXAMPLE 71

In a manner analogous to that described in the first paragraph of Example 1, from 3-[8-(acetoxymethyl)-6,7,8,9-tetrahydro-2-methoxy-pyrido[1,2-a]indol-10-yl]-4-(1-methyl-3-indolyl)furan-2,5-dione, there was prepared 3-[6,7,8,9-tetrahydro-8-(hydroxymethyl)-2-nethoxypyrido[1,2-a]indol-10-yl]-4-(1-methyl-3-indolyl)-1H-pyrrole-2,5-dione of melting point 195°–197° C.

The furandione starting material was prepared as follows:

a) 2 g of a 60% sodium hydride dispersion in mineral oil was washed with n-hexane by decantation and suspended in 100 ml of dimethylformamide under a nitrogen atmosphere. A solution of 10 g of ethyl 5-methoxyindole-2-carboxylate in 100 ml of dimethylformamide was added and the mixture was stirred. Then, 9.8 g of ethyl 4-bromobutyrate were added and the mixture was stirred for 2 hours. The mixture was cooled and treated with 50 ml of 1M hydrochloric acid and 400 ml of water. The mixture was extracted with diethyl ether and the combined extracts were washed with sodium chloride solution. The organic phase was dried and is evaporated. The obtained oil was dissolved in tetrahydrofuran and added to a mixture of 5.2 g of potassium t-butoxide in 200 ml of tetrahydrofuran under a nitrogen atmosphere. Then, the mixture was cooled and neutralized with 1M hydrochloric acid. Water was added and the mixture was extracted with diethyl ether. The combined extracts were washed with water and sodium chloride solution and then dried. Evaporation of the solvent and crystallization of the residue from ethyl acetate gave 6.7 g of ethyl 6,7-dihydro-9-hydroxy-2-methoxypyrido[1,2-a]indole-8-carboxylate of melting point 157°–160° C.

b) 5 g of the product of a) in 200 ml of ethanol were treated under a nitrogen atmosphere with 10 spoon spatula measures of Raney nickel and 100 ml of water. The suspension was heated at reflux, cooled and filtered. The solid was washed with ethyl acetate and volatile constituents were removed in a vacuum from the combined filtrate and washings. The aqueous suspension was extracted with ethyl acetate and the combined extracts were washed with sodium chloride solution and dried. Evaporation of the solvent and crystallization of the residue from methanol gave 2.41 g of ethyl 6,7,8,9-tetrahydro-2-methoxypyrido[1,2-a]indole-8-carboxylate of melting point 104°–105° C.

c) A solution of 2.3 g of the product of b) in 25 ml of tetrahydrofuran was added to a suspension of 260 mg of lithium aluminum hydride in 20 ml of tetrahydrofuran under a nitrogen atmosphere. Then, the mixture was treated with 10 ml of ethyl acetate followed by 20 ml of water. The mixture was acidified to pH 3 with 1M hydrochloric acid and extracted with diethyl ether. The combined extracts were washed with water and dried. Removal of the solvent by evaporation gave 1.85 g of 6,7,8,9-tetrahydro-2-methoxypyrido-[1,2-a]indole-8-methanol. A sample crystallized from ethyl acetate/n-hexane melted at 95°–96° C.

d) 1 g of the product of c) in 10 ml of pyridine was treated with 1.5 g of acetic anhydride. Then, the solvent was evaporated and the residue was partitioned between diethyl ether and 5% aqueous ammonium chloride. The organic phase was washed with sodium chloride solution, dried and evaporated. Crystallization of the residue from diethyl ether/ n-hexane gave 0.84 g of 8-acetoxymethyl-6,7,8,9-tetrahydro-2-methoxypyrido[1,2-a]indole of melting point 98°–100° C.

e) A suspension of 800 mg of the product of d) in 25 ml of diethyl ether was treated with 0.27 ml of oxalyl chloride under a nitrogen atmosphere. Then the solvent was evaporated, the residue was dissolved in 20 ml of dichloromethane and treated with 555 mg of N-methylindole-3-acetic acid and 0.8 ml of triethylamine. The mixture was stirred for 65 hours and the solvent was removed under reduced pressure. Chromatography of the residue on silica gel with ethyl acetate/n-hexane (1:1) gave 380 mg of 3-[8-(acetoxymethyl)-6,7,8,9-tetrahydro-2-methoxypyrido[1,2-a]indol-10-yl]-4-(1-methyl-3-indolyl)furan-2,5-dione. A sample crystallized from toluene/n-hexane melted at 131°–133° C. (decomposition).

EXAMPLE 72

In a manner analogous to that described in Example 2, from the product of Example 71, there was prepared 3-[8-(aminomethyl)-6,7,8,9-tetrahydro-1-methoxypyrido[1,2-a]indol-10-yl]-4-(1-methyl-3-indolyl)-1H-pyrrole-2,5-dione hydrochloride of melting point 235°–238° C. (decomposition).

EXAMPLE 73 a) A solution of 150 mg of the product of Example 20 in dichloromethane under a nitrogen atmosphere was treated with 135 mg of 1,1'-thiocarbonyldiimidazole. After 17 hours, the solution was washed with water and dried. The solvent was evaporated and the residue was crystallized from ethyl acetate to give 150 mg of 3-[1,2,3,4-tetrahydro-2-(1-imidazolylthiocarbonyl)pyrazino[1,2-a]indol-10-yl]-4-(1-methyl-3-indolyl)-1H-pyrrole-2,5-dione of melting point 244°–247° C.

b) A solution of 140 mg of the product of a) in 10 ml of dimethylformamide was treated with 20 ml of 33% aqueous ammonia. After 17 hours, the suspension was filtered and the solid was washed with water. The solid was dried to give 95 mg of 3-[1,2,3,4-tetrahydro-2-thiocarbamoylpyrazino-[1,2-a]indol-10-yl]-4-(1-methyl-3-indolyl)-1H-pyrrole-2,5-dione of melting point 278° C. (decomposition).

EXAMPLE 74

A solution of 150 mg of the product of Example 20 in 50 ml of dichloromethane was treated with 3 ml of acetic anhydride and 3 ml of triethylamine. After 17 hours, the solution was washed with water. The organic phase was dried and evaporated. The residue was dissolved in dichloromethane and treated with 0.08 ml of diethylamine. After 17 hours, the solution was evaporated. Crystallization of the residue from dichloromethane/n-hexane gave 80 mg of 3-[2-acetyl-1,2,3,4-tetrahydro-pyrazino[1,2-a]indol-10-yl]-4-(1-methyl-3-indolyl)-1H-pyrrole-2,5-dione of melting point 308°–310° C.

EXAMPLE 75

In a manner analogous to that described in Example 74, from the product of Example 2, there was prepared 3-[8-(acetamidomethyl)-6,7,8,9-tetrahydropyrido[1,2-a]indol-10-yl]-4-(1-methyl-3-indolyl)-1H-pyrrole-2,5-dione of melting point 270°–273° C.

EXAMPLE 76

A solution of 150 mg of the product of Example 20 in 40 ml of dichloromethane was treated with 40 mg of triethylamine and 44 mg of methanesulfonyl chloride. After 17 hours, the solution was washed with water. The organic phase was dried and evaporated. Chromatography of the residue on silica gel with ethyl acetate/n-hexane (2:1) and ethyl acetate gave 95 mg of 3-[1,2,3,4-tetrahydro-2-methanesulfonylpyrazino[1,2-a]indol-10-yl]-4-(1-methyl-3-indolyl)-1H-pyrrole-2,5-dione of melting point 298°–301° C. (decomposition).

EXAMPLE 77

3.0 g of the product of Example 1 were dissolved in 100 ml of tetrahydrofuran and the solution was added to a suspension of 1.8 g of lithium aluminum hydride in 50 ml of tetrahydrofuran at 0° C. Then, the mixture was heated at reflux for 16 hours. The mixture was cooled, treated with 10 ml of water and extracted with dichloromethane. The combined dichloromethane extracts were washed with aqueous sodium bicarbonate solution, dried and concentrated to give a solid. Chromatography on silica gel with dichloromethane/methanol (95:5) gave a solid which was purified further by chromatography to give a) 400 mg of 1,5-dihydro-3-[6,7,8,9-tetrahydro-8-(hydroxymethyl)pyrido[1,2-a]indol-10-yl]-4-(1-methyl-3-indolyl)-2H-pyrrole-2-one of melting point 205°–207° C. There were also obtained b) 160 mg of 1,5-dihydro-4-[6,7,8,9-tetrahydro-8-(hydroxymethyl)pyrido[1,2-a]indol-10-yl]-3-(1-methyl-3-indolyl)-2H-pyrrole-2-one of melting point 201°–203° C.

EXAMPLE 78

In a manner analogous to that described in the first paragraph of Example 1, from 0.5 g of 3-[8-(acetoxymethyl)-6,7,8,9-tetrahydropyrido[1,2-a]indol-10-yl]-4-(3-trifluoromethylphenyl)furan-2,5-dione, there were obtained 110 mg of 3-[6,7,8,9-tetrahydro-8-(hydroxymethyl)pyrido[1,2-a]indol-10-yl]-4-(3-trifluoromethylphenyl)-1H-pyrrole-2,5-dione solid of melting point 77°–79° C.

The furandione starting material was prepared as follows:

1.7 g of oxalyl chloride were added to a cold (0°–4° C.) solution of 3.0 g of 8-(acetoxymethyl)-6,7,8,9-tetrahydropyrido[1,2-a]indole in 50 ml of dichloromethane. After 2 hours, the solvent was evaporated and the residue was dissolved in dichloromethane. The solution was added to a solution of 2.7 g of (α,α,α-trifluoro-m-tolyl)acetic acid and 3.2 g of triethylamine in 70 ml of dichloromethane. The mixture was stirred for 16 hours and then concentrated. The residue was chromatographed on silica gel with dichloromethane/methanol (95:5). There were obtained 700 mg of 3-[8-(acetoxymethyl)-6,7,8,9-tetrahydropyrido[1,2-a]indol-10-yl]-4-(3-trifluoromethylphenyl)furan-2,5-dione of melting point 176°–177°–C.

EXAMPLE 79

In a manner analogous to that described in the first paragraph of Example 1, from 1.0 g of 3-[8-(acetoxymethyl)-6,7,8,9-tetrahydropyrido[1,2-a]indol-10-yl]-4-(4-methoxyphenyl)furan-2,5-dione, there were obtained 150 mg of 3-[6,7,8,9-tetrahydro-8-(hydroxymethyl)pyrido[1,2-a]indol-10-yl]-4-(4-methoxyphenyl)-1H-pyrrole-2,5-dione of melting point 228° C. (decomposition).

The furandione starting material was prepared as follows:

1.7 g of oxalyl chloride were added to a cold (0°–4° C.) solution of 3.0 g of 8-(acetoxymethyl)-6,7,8,9-tetrahydropyrido[1,2-a]indole in 50 ml of dichloromethane. After 2 hours, the solvent was evaporated and the residue was dissolved in dichloromethane. This solution was added to a solution of 2.24 g of p-methoxyphenylacetic acid and 3.2 g of triethylamine in 70 ml of dichloromethane. The mixture was stirred for 16 hours and then concentrated. Chromatography of the residue on silica gel with dichloromethane/methanol (95:5) gave 2 g of 3-[8-(acetoxymethyl)-6,7,8,9-tetrahydropyrido[1,2-a]indol-10-yl]-4-(4-methoxyphenyl)furan-2,5-dione of melting point 79°–82° C.

EXAMPLE 80

In a manner analogous to that described in the first paragraph of Example 1, from 0.8 g of 3-[8-(acetoxymethyl)-6,7,8,9-tetrahydropyrido[1,2-a]indol-10-yl]-4-(2-chlorophenyl)furan-2,5-dione, there were obtained 120 mg of 3-(2-chlorophenyl)-4-[6,7,8,9-tetrahydro-8-(hydroxymethyl)pyrido[1,2-a]indol-10-yl]-1H-pyrrole-2,5-dione of melting point 232°–233° C.

The furandione starting material was prepared as follows:

2.2 g of oxalyl chloride were added to an ice-cold solution of 4 g of 8-(acetoxymethyl)-6,7,8,9-tetrahydropyrido[1,2-a]indole in 50 ml of dichloromethane. After 2 hours, the solvent was evaporated and the residue was dissolved in dichloromethane. This solution was added to a solution of 3.0 g of 2-chlorophenylacetic acid and 4.0 g of triethylamine in dichloromethane. The mixture was stirred for 16 hours and then concentrated. Chromatography of the residue on silica gel with dichloromethane/methanol (95:5) yielded 0.9 g of 3-[8-(acetoxymethyl)-6,7,8,9-tetrahydropyrido[1,2-a]indol-10-yl]-4-(2-chlorophenyl)furan-2,5-dione of melting point 168°–171° C.

EXAMPLE 81

In a manner analogous to that described in Example 51, from 80 mg of the product of Example 78, there were obtained 30 mg of 3-[8-(aminomethyl)-6,7,8,9-tetrahydropyrido[1,2-a]indol-10-yl]-4-(3-trifluoromethylphenyl)-1H-pyrrole-2,5-dione of melting point 202°–204° C.

EXAMPLE 82

In a manner analogous to that described in Example 51, from 100 mg of the product of Example 79, there were obtained 88 mg of 3-[8-(aminomethyl)-6,7,8,9-tetrahydropyrido[1,2-a]indol-10-yl]-4-(4-methoxyphenyl)-1H-pyrrole-2,5-dione of melting point 195°–196° C.

EXAMPLE 83

In a manner analogous to that described in Example 53, from 80 mg of the product of Example 80, there were obtained 57 mg of 3-[8-(aminomethyl)-6,7,8,9-tetrahydropyrido[1,2-a]indol-10-yl]-4-(2-chlorophenyl)-1H-pyrrole-2,5-dione of melting point 206°–208° C. (decomposition).

The following Examples illustrate typical pharmaceutical preparations containing compounds provided by the invention:

EXAMPLE A

Tablets containing the following ingredients may be produced in a conventional manner:

| Ingredient | Per tablet |
| --- | --- |
| A compound of formula I | 5.0 mg |
| Lactose | 125.0 mg |
| Maize starch | 75.0 mg |
| Talc | 4.0 mg |
| Magnesium stearate | 1.0 mg |
| Tablet weight | 210.0 mg |

EXAMPLE B

Capsules containing the following ingredients may be produced in a conventional manner:

| Ingredient | Per capsule |
| --- | --- |
| A compound of formula I | 10.0 mg |
| Lactose | 165.0 mg |
| Maize starch | 20.0 mg |
| Talc | 5.0 mg |
| Capsule fill weight | 200.0 mg |

We claim:

1. A compound of the formula

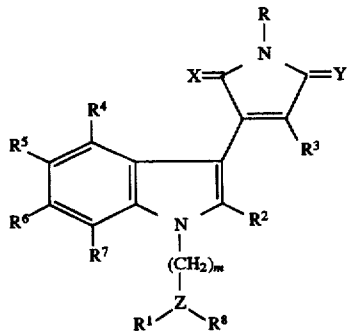

wherein R is hydrogen or hydroxy, $R^1$ and $R^2$ taken together are —$CH_2$— and $R^7$ is hydrogen; $R^3$ is unsubstituted phenyl, naphthyl, 3-benzothienyl, 3-benzofuranyl or 3-indolyl or phenyl, naphthyl, 3-benzothienyl, 3-benzofuranyl or 3-indolyl substituted with one substituent selected from halogen, alkyl, hydroxy, alkoxy, haloalkyl, nitro, amino, acylamino, alkylthio, alkylsulfinyl and alkylsulfonyl; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, amino-carbonylamino, isothiocyanato, alkylcarbonyloxy, alkylsulfonyloxy or arylsulfonyloxy, or a group of the formula —U—C(V)—W; U is S or NH; V is NH, $NNO_2$, NCN, $CHNO_2$; W is amino, monoalkylamino or dialkylamino; one of X and Y is O and the other is O or (H,H); Z is CH; m is 1 or 2 and p and q are, independently, an integer from 0 to 5;

or a pharmaceutically acceptable salt of an acidic compound of formula I with a base or of a basic compound of formula I with an acid.

2. A compound according to claim 1, wherein R is hydrogen, and $R^9$ is hydrogen, alkylcarbonyl, cyano, amidino, alkoxycarbonyl, alkylsulfonyl, aminocarbonyl or aminothiocarbonyl and $R^{10}$ is hydroxy, alkoxy, halogen, amino, monoalkylamino, dialkylamino, trialkylamino, azido, acylamino, alkylsulfonylamino, arylsulfonylamino, alkylthio, aminocarbonylamino, isothiocyanato, alkylcarbonyloxy, alkylsulfonyloxy or arylsulfonyloxy or a group of the formula —U—C(V)—W.

3. A compound according to claim 1, wherein $R^3$ is 1-methyl-3-indolyl.

4. A compound according to claim 3, wherein $R^4$, $R^5$ and $R^6$ are hydrogen.

5. A compound according to claim 4, wherein $R^8$ is a group of the formula —$(CH_2)_q$—$R^{10}$.

6. A compound according to claim 5, wherein q stands for 1 or 2.

7. A compound according to claim 6, wherein $R^{10}$ is hydroxy, amino, monoalkylamino, dialkylamino, trialkylamino, azido, acylamino, alkylcarbonyloxy or alkylsulfonyloxy or a group of the formula —U—C(V)—W.

8. A compound according to claim 7, wherein U is S, V is NH and W is amino.

9. A compound according to claim 8, wherein X and Y and O.

10. A compound according to claim 1, selected from the group consisting of

3-[8-(aminomethyl)-6,7,8,9-tetrahydropyrido[1,2-a]indol-10-yl]-4-(1-methyl-3-indolyl)-1H-pyrrole-2,5-dione, 3-[7-(amidinothiomethyl)-6,7,8,9-tetrahydropyrido[1,2-a]indol-10-yl]-4-(1-methyl-3-indolyl)-1H-pyrrole-2,5-dione, 3-[6,7,8,9-tetrahydro-8-[(dimethylamino)methyl]pyrido[1,2-a]indol-10-yl]-4-(1-methyl-3-indolyl)-1H-pyrrole-2,5-dione, or a pharmaceutically acceptable acid addition salt thereof.

11. A compound of the formula

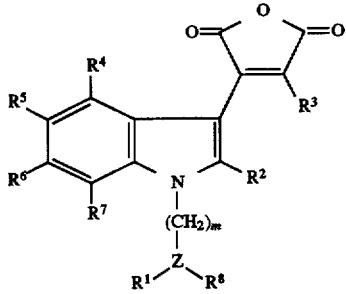

wherein $R^1$ and $R^2$ taken together are —$CH_2$— and $R^7$ is hydrogen; $R^3$ is unsubstituted phenyl, naphthyl, 3-benzothienyl, 3-benzofuranyl or 3-indolyl or phenyl, naphthyl, 3-benzothienyl, 3-benzofuranyl or 3-indolyl substituted with one substituent selected from halogen, alkyl, hydroxy, alkoxy, haloalkyl, nitro, amino, acylamino, alkylthio, alkylsulfinyl and alkylsulfonyl; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, amino-carbonylamino, isothiocyanato, alkylcarbonyloxy, alkylsulfonyloxy or arylsulfonyloxy, or a group of the formula —U—C(V)—W; U is S or NH; V is NH, $NNO_2$, NCN, $CHNO_2$; W is amino, monoalkylamino or dialkylamino; Z is CH; m is 1 or 2 and p and q are, independently, an integer from 0 to 5.

12. The compound of claim 1, 3-[6,7,8,9-tetrahydropyrido-[1,2-a]indol-10-yl]-4-(1-methyl-3-indolyl)-1H-pyrrole-2,5-dione.

13. A pharmaceutical composition comprising an effective amount of a compound of the formula

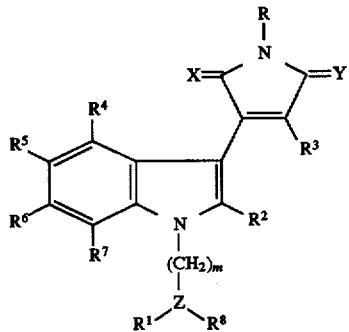

wherein R is hydrogen or hydroxy, $R^1$ and $R^2$ taken together are —$CH_2$— and $R^7$ is hydrogen; $R^3$ is unsubstituted phenyl, naphthyl, 3-benzothienyl, 3-benzofuranyl or 3-indolyl or phenyl, naphthyl, 3-benzothienyl, 3-benzofuranyl or 3-indolyl substituted with one substituent selected from halogen, alkyl, hydroxy, alkoxy, haloalkyl, nitro, amino, acylamino, alkylthio, alkylsulfinyl and alkylsulfonyl; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, amino-carbonylamino, isothiocyanato, alkylcarbonyloxy, alkylsulfonyloxy or arylsulfonyloxy, or a group of the formula —U—C(V)—W; U is S or NH; V is NH, $NNO_2$, NCN, $CHNO_2$; W is amino, monoalkylamino or dialkylamino; one of X and Y is O and the other is O or (H,H); Z is CH; m is 1 or 2 and p and q are, independently, an integer from 0 to 5;

or a pharmaceutically acceptable salt of an acidic compound of formula I with a base or of a basic compound of formula I with an acid, and an inert carrier material.

14. A pharmaceutical composition according to claim 13, wherein R is hydrogen, and $R^9$ is hydrogen, alkylcarbonyl, cyano, amidino, alkoxycarbonyl, alkylsulfonyl, aminocarbonyl or aminothiocarbonyl and $R^{10}$ is hydroxy, alkoxy, halogen, amino, monoalkylamino, dialkylamino, trialkylamino, azido, acylamino, alkylsulfonylamino, arylsulfonylamino, alkylthio, aminocarbonylamino, isothiocyanato, alkylcarbonyloxy, alkylsulfonyloxy or arylsulfonyloxy or a group of the formula —U—C(V)—W.

15. A method of inhibiting protein kinase which comprises administering an effective amount of a compound of the formula

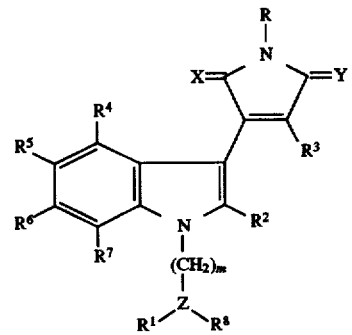

wherein R is hydrogen or hydroxy, $R^1$ and $R^2$ taken together are —$CH_2$— and $R^7$ is hydrogen; $R^3$ is unsubstituted phenyl, naphthyl, 3-benzothienyl, 3-benzofuranyl or 3-indolyl or phenyl, naphthyl, 3-benzothienyl, 3-benzofuranyl or 3-indolyl substituted with one substituent selected from halogen, alkyl, hydroxy, alkoxy, haloalkyl, nitro, amino, acylamino, alkylthio, alkylsulfinyl and alkylsulfonyl; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, amino-carbonylamino, isothiocyanato, alkylcarbonyloxy, alkylsulfonyloxy or arylsulfonyloxy, or a group of the formula —U—C(V)—W; U is S or NH; V is NH, NNO$_2$, NCN, CHNO$_2$; W is amino, monoalkylamino or dialkylamino; one of X and Y is O and the other is O or (H,H); Z is CH; m is 1 or 2 and p and q are, independently, an integer from 0 to 5; or a pharmaceutically acceptable salt of an acidic compound of formula I with a base or of a basic compound of formula I with an acid.

16. A method according to claim 15, wherein R is hydrogen, and R$^9$ is hydrogen, alkylcarbonyl, cyano, amidino, alkoxycarbonyl, alkylsulfonyl, aminocarbonyl or aminothiocarbonyl and R$^{10}$ is hydroxy, alkoxy, halogen, amino, monoalkylamino, dialkylamino, trialkylamino, azido, acylamino, alkylsulfonylamino, arylsulfonylamino, alkylthio, aminocarbonylamino, isothiocyanato, alkylcarbonyloxy, alkylsulfonyloxy or arylsulfonyloxy or a group of the formula —U—C(V)—W.

17. A pharmaceutical composition of claim 13, wherein the compound of formula I is 3-[6,7,8,9-tetrahydro-pyrido-[1,2-a]indol-10-yl]-4-(1-methyl-3-indolyl)-1H-pyrrole-2,5-dione.

18. A method according to claim 15, wherein the compound of formula I is 3-[6,7,8,9-tetrahydro-pyrido-[1,2-a]indol-10-yl]-4-(1-methyl-3-indolyl)-1H-pyrrole-2,5-dione.

* * * * *